(12) United States Patent
Jiang et al.

(10) Patent No.: US 11,680,285 B2
(45) Date of Patent: *Jun. 20, 2023

(54) HOOKED PROBE, METHOD FOR LIGATING NUCLEIC ACID AND METHOD FOR CONSTRUCTING SEQUENCING LIBRARY

(71) Applicant: MGI TECH CO., LTD., Guangdong (CN)

(72) Inventors: Yuan Jiang, Guangdong (CN); Yang Xi, Guangdong (CN); Wenwei Zhang, Guangdong (CN); Pengjuan Liu, Guangdong (CN); Xia Zhao, Guangdong (CN); Qiaoling Li, Guangdong (CN); Hanjie Shen, Guangdong (CN); Yongwei Zhang, Guangdong (CN); Radoje Drmanac, Guangdong (CN)

(73) Assignee: MGI TEGH GO., LTD., Guangdong (CN)

( * ) Notice: Subject to any disclaimer, the term of this patent is extended or adjusted under 35 U.S.C. 154(b) by 221 days.

This patent is subject to a terminal disclaimer.

(21) Appl. No.: 16/762,898

(22) PCT Filed: Nov. 9, 2017

(86) PCT No.: PCT/CN2017/110252
§ 371 (c)(1),
(2) Date: May 8, 2020

(87) PCT Pub. No.: WO2019/090621
PCT Pub. Date: May 16, 2019

(65) Prior Publication Data
US 2021/0172009 A1    Jun. 10, 2021

(51) Int. Cl.
*C12Q 1/6834* (2018.01)
*C12Q 1/6855* (2018.01)
*C12Q 1/6876* (2018.01)

(52) U.S. Cl.
CPC ......... *C12Q 1/6834* (2013.01); *C12Q 1/6855* (2013.01); *C12Q 1/6876* (2013.01)

(58) Field of Classification Search
CPC ... C12Q 1/6834; C12Q 1/6855; C12Q 1/6876
See application file for complete search history.

(56) References Cited

U.S. PATENT DOCUMENTS

| | | | | |
|---|---|---|---|---|
| 11,091,791 B2 * | 8/2021 | Jiang | ............ | C12Q 1/6806 |
| 2014/0155274 A1 * | 6/2014 | Xie | ............ | C12N 15/1065 506/2 |
| 2016/0257993 A1 * | 9/2016 | Fu | ............ | C12Q 1/6844 |
| 2016/0304948 A1 * | 10/2016 | Lee | ............ | C12Q 1/6855 |
| 2016/0340740 A1 | 11/2016 | Zhang | | |
| 2018/0245132 A1 * | 8/2018 | Jiang | ............ | C12Q 1/6806 |

FOREIGN PATENT DOCUMENTS

| CN | 106232833 | 12/2016 |
|---|---|---|
| CN | 107236729 | 10/2017 |
| WO | 2017075265 | 5/2017 |

OTHER PUBLICATIONS

Kirino and Honda, Dumbbell—PCR: a method to quantify specific small RNA variants with a single nucleotide resolution terminal sequence, Nucleic Acids Research, 2015, 43(12), 1-12 (Year: 2015).*
Broude et al., Nucleic Acids Research 29(19): e92 (Year: 2001).*
Odell et al., Nucleic Acids Research 31(17) : 5090-5100 (Year: 2003).*
International Search Report in the international application No. PCT/CN2017/110252, dated Aug. 15, 2018 with English translation by WIPO.
Written Opinion of the International Searching Authority in the international application No. PCT/CN2017/110252, dated Aug. 9, 2018, with English translation provided by Google Translate.

* cited by examiner

*Primary Examiner* — Ethan C Whisenant
(74) *Attorney, Agent, or Firm* — Ladas & Parry, LLP

(57) ABSTRACT

Provided are a hooked probe, a method for ligating a nucleic acid and a method for constructing a sequencing library. The hooked probe comprises a target specific area and a hooked area ligated thereto; the target specific area comprises a sequence complementarily paired with at least part of the single chain of the nucleic acid fragment to be ligated; the hooked area comprises a sequence unpaired with the nucleic acid fragment; the end of the hooked area is a ligatable end; and the ligatable end can ligate the end of the single chain of the nucleic acid fragment.

14 Claims, 7 Drawing Sheets

Specification includes a Sequence Listing.

SEQUENCE LISTING

```
<160> NUMBER OF SEQ ID NOS: 20

<210> SEQ ID NO 1
<211> LENGTH: 90
```

<212> TYPE: DNA
<213> ORGANISM: Artificial Sequence
<220> FEATURE:
<223> OTHER INFORMATION: Synthetic Sequence

<400> SEQUENCE: 1
ctcatgccct tcggctgcct cctggactat gtccgggaac acaaagacaa tattggctcc    60
cagtacctgc tcaactggtg tgtgcagatc    90

<210> SEQ ID NO 2
<211> LENGTH: 59
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (46)..(51)
<223> OTHER INFORMATION: n is a, c, g, or t

<400> SEQUENCE: 2
caggaggcag ccgaagggca gaacgacatg gctacgatcc gacttnnnnn ncatttcat    59

<210> SEQ ID NO 3
<211> LENGTH: 46
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (41)..(46)
<223> OTHER INFORMATION: n is a, c, g, or t

<400> SEQUENCE: 3
nnnnnnnnnn nnnnngaacg acatggctac gatccgactt nnnnnn    46

<210> SEQ ID NO 4
<211> LENGTH: 46
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (41)..(46)
<223> OTHER INFORMATION: n is a, c, g, or t

<400> SEQUENCE: 4
nnnnnnnnnn nnnnngaacg acatggctac gatccgactt nnnnnn    46

<210> SEQ ID NO 5
<211> LENGTH: 42
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (26)..(42)
<223> OTHER INFORMATION: n is a, c, g, or t

<400> SEQUENCE: 5
atgctgacgg tcaagtggtc ttaggnnnnn nnnnnnnnnn nn    42

<210> SEQ ID NO 6
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 6
atgctgacgg tcaagtggtc ttaggaggac agcggctgcg atcac    45

<210> SEQ ID NO 7
<211> LENGTH: 60
<212> TYPE: DNA
<213> ORGANISM: Artificial Sequence
<220> FEATURE:
<223> OTHER INFORMATION: Synthetic Sequence

<400> SEQUENCE: 7
atgctgacgg tcaagtggtc ttaggtatac ctttgttgtt acctttaaat gcaaagttaa    60

<210> SEQ ID NO 8
<211> LENGTH: 60
<212> TYPE: DNA
<213> ORGANISM: Artificial Sequence
<220> FEATURE:
<223> OTHER INFORMATION: Synthetic Sequence

<400> SEQUENCE: 8
atgctgacgg tcaagtggtc ttagggtggt gtagatatga tcaaaaggg attcaattgc    60

<210> SEQ ID NO 9
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 9
atgctgacgg tcaagtggtc ttagggctgc aggagaaaca gtctc    45

<210> SEQ ID NO 10
<211> LENGTH: 49
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(17)
<223> OTHER INFORMATION: n is a, c, g, or t
<220> FEATURE:
<221> NAME/KEY: misc_feature
<222> LOCATION: (43)..(48)
<223> OTHER INFORMATION: n is a, c, g, or t

<400> SEQUENCE: 10
nnnnnnnnnn nnnnnnngaa cgacatggct acgatccgac ttnnnnnnt    49

<210> SEQ ID NO 11
<211> LENGTH: 66
<212> TYPE: DNA
<213> ORGANISM: Artificial Sequence
<220> FEATURE:
<223> OTHER INFORMATION: Synthetic Sequence

```
<220> FEATURE:
<221> NAME/KEY: misc_feature
<222> LOCATION: (60)..(65)
<223> OTHER INFORMATION: n is a, c, g, or t

<400> SEQUENCE: 11
gaattattta acaattatga ctattcattt aggcgaacga catggctacg atccgactt n     60 nnnnnt                                                                 66

<210> SEQ ID NO 12
<211> LENGTH: 52
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (46)..(51)
<223> OTHER INFORMATION: n is a, c, g, or t

<400> SEQUENCE: 12
ggcagaagtc ttgcccacat gaacgacatg gctacgatcc gacttnnnnn nt             52

<210> SEQ ID NO 13
<211> LENGTH: 53
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (47)..(52)
<223> OTHER INFORMATION: n is a, c, g, or t

<400> SEQUENCE: 13
catttaactg gaatccgacc cgaacgacat ggctacgatc cgacttnnnn nnt            53

<210> SEQ ID NO 14
<211> LENGTH: 52
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (46)..(51)
<223> OTHER INFORMATION: n is a, c, g, or t

<400> SEQUENCE: 14
caacaattct gggaaccacc gaacgacatg gctacgatcc gacttnnnnn nt             52

<210> SEQ ID NO 15
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 15
cacagaacga catggctacg atccgact                                         28

<210> SEQ ID NO 16
<211> LENGTH: 56
<212> TYPE: DNA
<213> ORGANISM: Artificial Sequence
<220> FEATURE:
<223> OTHER INFORMATION: Synthetic Sequence
```

```
<400> SEQUENCE: 16
tgtgagccaa ggagttgact ttacttgtct tcctaagacc acttgaccgt cagcat         56

<210> SEQ ID NO 17
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 17
gctacgatcc gactt                                                       15

<210> SEQ ID NO 18
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 18
aagtcggatc gtagccatgt cgttc                                            25

<210> SEQ ID NO 19
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 19
gaacgacatg gctacga                                                     17

<210> SEQ ID NO 20
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 20
tgtgagccaa ggagttg                                                     17
```

HOOKED PROBE, METHOD FOR LIGATING NUCLEIC ACID AND METHOD FOR CONSTRUCTING SEQUENCING LIBRARY

CROSS-REFERENCE TO RELATED APPLICATIONS

The present application is the U.S. National Phase Application of PCT Application No. PCT/CN2017/110252 filed on Nov. 9, 2017, the disclosure of which is incorporated herein by reference in its entirety.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 632634-SequenceListing1.txt, the date of creation of the ASCII text file is May 8, 2020, and the size of the ASCII text file is 5087 bytes.

TECHNICAL FIELD

The present invention relates to the technical field of molecular biology, particularly to a hook probe, a nucleic acid ligation method and a sequencing library construction method.

BACKGROUND OF THE INVENTION

High-throughput sequencing technology represents a revolutionary change to traditional sequencing. It can sequence hundreds of thousands to millions of DNA molecules at a time to allow for a detailed and comprehensive analysis of the transcriptome and genome of a species to discover phenotype-related genes or genetic variation sites, providing a theoretical basis for scientific researches and applications. A high-throughput sequencing library is a set of DNA or cDNA sequence fragments that are formed by a series of biochemical reactions by adding known artificially synthesized sequences to fragmented DNA or RNA, and that can be enlarged by way of amplification. The known artificially synthesized sequence added is usually called an adapter, which mainly serves to amplify the library and provide a complementary sequence for sequencing primer hybridization. The basic process of library construction includes nucleic acid extraction, nucleic acid fragmentation (no fragmentation is required in case of free DNAs), end repair and modification of fragmented nucleic acids, adapter ligation, fragment amplification or no need for amplification. According to different research purposes and different types of starting samples, the library construction processes are slightly altered on the basis of the above basic process. For example, library construction of free DNAs does not entail DNA fragmentation, library construction of RNAs requires the additional processing of reverse transcription into cDNAs, and library construction of target regions requires enriching for the target region sequences from DNAs or RNAs by way of hybridization or amplification.

In the past 10 years, the cost of high-throughput sequencing has dropped sharply in the mode of super-Moore's law, allowing high-throughput sequencing to expand its application from scientific researches to more fields such as clinical testing, and especially to provide precision medicine with novel and reliable detection methods. The techniques for sequencing DNA, RNA, cfDNA, or ctDNA target regions have the advantages of multiple detection sites, large sample throughput, low economic cost, and higher detection sensitivity due to the only need for the genes of interest to be subjected to high-depth sequencing, and are thus widely used in disease diagnosis and targeted drug therapy. Providing efficient, fast, accurate, reliable, and affordable library construction and sequencing technologies constitutes a key breakthrough for the application of high-throughput sequencing in precision medicine.

Two main types of library construction technologies exist for target region enrichment. The first type is based on probe hybridization technologies, which are subdivided into solid phase hybridization and liquid phase hybridization, the latter being extensively used currently, for example, the RNA probe liquid phase hybridization technology available from Agilent Technologies Inc., the DNA probe liquid phase hybridization technology available from Roche NimbleGen, and transposase fragmentation in combination with DNA probe liquid phase hybridization technology available from Illumina Inc. The second type is amplification-based technologies, which are subdivided into the single pair amplification followed by pooling technology and the multiplex amplification technology, the latter being currently more widely used, such as the Ion Torrent AmpliSeq multiplex PCR technology available from Life Technologies.

Probe liquid phase hybridization and capture technology is very suitable for a high-throughput sequencing library construction process that requires highly parallel sample preparation. This technology uses blocking nucleic acids such as Cot-1 DNA and/or sequence-specific blocking oligonucleotides to reduce non-specific hybridization and enhance the specificity of the hybridization reaction between a probe and a sample nucleic acid. However, commonly used hybridization and capture methods require a very long hybridization time to achieve equilibrium and/or to achieve effective capture and enrichment of target nucleic acids. Nevertheless, these methods still suffer from contamination by at least about 40% non-target regions. Moreover, during hybridization, washing, and elution, or in the reaction process at the upstream of the hybridization step (such as, adapter ligation) or downstream of the hybridization step (such as binding of a biotin-labeled hybridization complex to streptovidin beads), there exists the risk of random loss of the target sequence. In addition, the reagents used in the methods (such as probes, blocking reagents, streptovidin beads, etc.) are expensive without much room for price reduction.

The multiplex PCR technology can more efficiently and specifically enrich for target region sequences, with the cost being lower than that of the probe liquid phase hybridization and capture technology, but it is not conducive to the enrichment of the target regions of small-fragment cfDNAs that have been naturally fragmented.

SUMMARY OF THE INVENTION

The present invention provides a hook probe, a nucleic acid ligation method and a sequencing library construction method. The hook probe allows addition of a stretch of known tool sequence at a single-stranded end of a nucleic acid fragment to be ligated, and use of the stretch of known tool sequence to perform subsequent operations and reactions can accomplish different applications.

According to a first aspect, the present invention provides a hook probe, which comprises a target-specific region and a hook region the target-specific region comprising a sequence complementary to at least part of a single strand of a nucleic acid fragment to be ligated, the hook region comprising a sequence not complementary to the nucleic acid fragment, and an end of the hook region being a ligatable end, which can be ligated to a single-stranded end of the nucleic acid fragment.

According to a second aspect, the present invention provides a kit, which comprises the hook probe according to the first aspect, and optionally, further comprises at least one ligase, the ligase being useful for ligating the ligatable end of the hook probe to an end of the nucleic acid fragment to be ligated.

According to a third aspect, the present invention provides a use of the hook probe according to the first aspect in nucleic acid sequencing library construction.

According to a fourth aspect, the present invention provides a nucleic acid ligation method, comprising annealing and hybridizing the hook probe according to the first aspect to a denatured nucleic acid fragment to be ligated; and ligating the ligatable end of the hook probe to a single-stranded end of the nucleic acid fragment in the presence of a ligase.

According to a fifth aspect, the present invention provides a method of nucleic acid sequencing library construction, comprising a step of annealing and hybridizing the hook probe according to the first aspect to a denatured nucleic acid fragment to be ligated; and a step of ligating the ligatable end of the hook probe to a single-stranded end of the nucleic acid fragment in the presence of a ligase.

With ingenious design of the hook probe and cooperation of a ligase, the present invention achieves rapid hybridization and capture of a nucleic acid fragment (such as a target sequence) to be ligated and addition of a stretch of known tool sequence at the same time, and by ingeniously designing and using the known tool sequence to perform subsequent operations and reactions, the present invention can accomplish different applications.

In particular, the present invention can be suitable for a wide range of sample types, detection types and application fields (not limited to high throughput library construction, but can also be used in molecular cloning and synthetic biology, among other fields). It is anticipated that the realization of the present invention will greatly result in process simplification, time reduction and cost saving, will break through the limitations of applicable sample types, will benefit a variety of scientific research applications and kit packages, and will have very promising market potential and prospect.

DETAILED DESCRIPTION OF THE INVENTION

Figure 1:
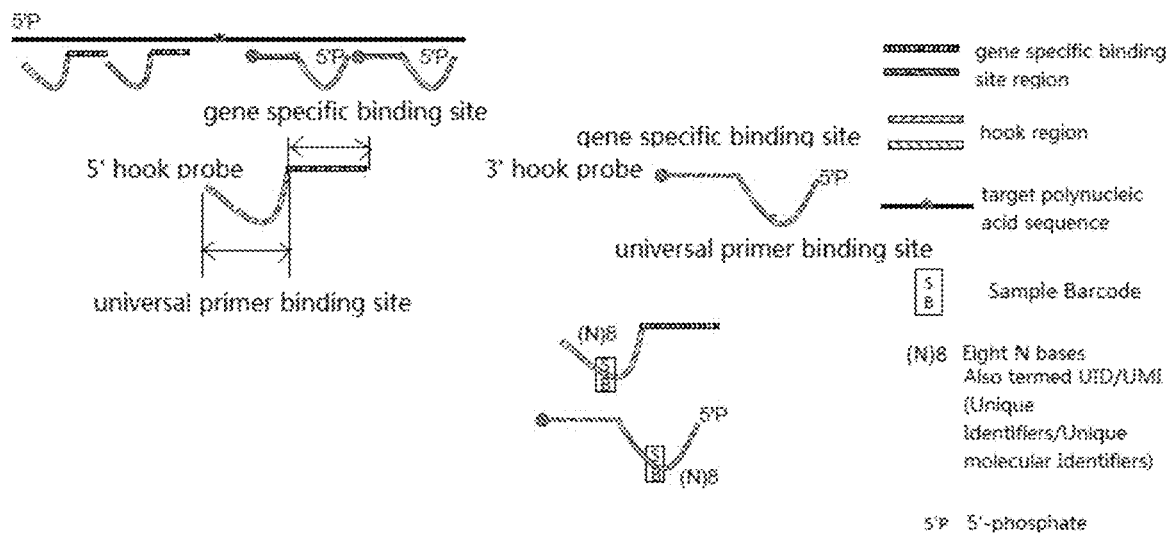
FIG. 1 shows a schemic diagram of the makeup of the target-specific 5' hook probe and 3' hook probe.

The present application will be further described in detail below with reference to the accompanying drawings. In the following embodiments, many details are described so that the present application will be better understood. However, those skilled in the art can readily recognize that some of the features may be omitted, or replaced by other elements, materials, or methods, depending on different situations. In some cases, some operations related to the present application are not shown or described in this specification, so as to avoid overwhelming the core part of the present application with excessive description. Detailed description of these relevant operations is not necessary for those skilled in the art, who can have a complete knowledge of the relevant operations in light of the description in the specification and the general technical knowledge in the art.

The present invention proposes a hook probe (or termed as "hook nucleic acid probe"). Taking advantage of the hook probe of the present invention and the basic principle of intermolecular single strand ligation reaction, a nucleic acid fragment can be rapidly captured and an adapter can be added at the same time. The present invention proposes a series of technical solutions generated on the basis of the hook probe and the basic principle, including but not limited to the oligonucleotide sequence composition, enzymes and reagent components, reaction conditions, process steps, etc., required for implementing the technical solutions.

The basic principle of the present invention is as follows. Under suitable reaction conditions, a nucleic acid fragment, such as a target region nucleic acid single-stranded fragment (containing a phosphate group at the 5' end or a hydroxy group at the 3' end), and a target-specific hook probe (containing a phosphate group at the 5' end or a hydroxy group at the 3' end) with part of the sequence thereof being complementary to the target region nucleic acid single-stranded fragment, will form a hybridization complex. Under the catalysis of a certain ligase, the intermolecular single strand ligation product of the non-complementary regions (the 5' end of the target region nucleic acid single strand and the 3' end of the hook probe) of the hybridization complex is produced in a higher proportion than the intra-molecular single strand circularization product of the target region nucleic acid single-stranded fragment, and the single strand intermolecular product formed between the single strands without complementary regions occurs in a very low proportion.

The present invention relates to the following basic concepts: hook probe, nucleic acid fragment (such as target region nucleic acid fragment), and ligase. The present invention has at least one of the following advantages: suitable templates not limited by the type of the samples, fast hybridization, no need for the additional step of adding an adapter, simple procedure, short reaction time, low cost, and wide fields of application.

An embodiment of the present invention provides a hook probe, which comprises a target-specific region and a hook region, the target-specific region comprising a sequence complementary to at least part of a single strand of a nucleic acid fragment to be ligated, the hook region comprising a sequence not complementary to the nucleic acid fragment, and an end of the hook region being a ligatable end, which can be ligated to a single-stranded end of the nucleic acid fragment.

The following presents a detailed description of the specific definitions of some basic concepts and the constituent elements thereof.

1. Hook Probe

A hook probe may be a 5' hook probe or a 3' hook probe. FIG. 1 shows a schematic view of the hook probe. The hook probe provided in the embodiments of the present invention includes a target specific region (TSR) and a hook region (HR). A sequence of the target specific region (that is, the gene specific binding site shown in FIG. 1) is complementary to a sequence near a nucleic acid fragment to be ligated (such as a target sequence) in a sample, and thus performs the function of hybridization and capture. The hook region of the 5' hook probe may include a universal primer binding site, a unique molecular identifier, a sample barcode, a cell barcode, other useful elements, or any combination thereof. Similarly, the hook region of the 3' hook probe may include a universal primer binding site, a unique molecular identifier, a sample barcode, a cell barcode, other useful elements, or any combination thereof. In particular, the hook region may also be designed as a random sequence to be used in a library construction protocol not based on sequence capture (such as whole-genome library construction). The universal primer binding site of the hook probe may participate in the subsequent intermolecular ligation reaction of the hybridization complex and the PCR amplification or PCR-free library construction of the hook ligation product. The sample barcode and/or unique molecular identifier of the hook probe are intended for use in identifying different samples and/or target sequence fragments.

In some embodiments, the 5' hook probe has the following structure: 5'-(target specific region)-(hook region)-3'. Preferably, the 5' hook probe has the structure of 5'-(target specific region)-(unique molecular identifier and/or sample barcode)-(universal primer binding site)-3'. In some embodiments, the 3' hook probe has the following structure: 5'-(hook region)-(target specific region)-3'. Preferably, the 5' hook probe has the structure of 5'-(universal primer binding site)-(unique molecular identifier and/or sample barcode)-(target specific region)-3'.

The biochemical components of the hook probe may be deoxyribonucleic acids or ribonucleic acids, or may be a mixture of deoxyribonucleic acids and ribonucleic acids.

1.1 Target Specific Region (TSR)

The target specific region in the hook probe may have any suitable length and sequence for target-specific hybridization to a target nucleic acid in a reaction mixture containing both target and non-target nucleic acids. The length of the target specific region is generally less than 200 nucleotides.

It should be noted that the target-specific region is not solely dedicated to hybridization with the target nucleic acids, which is only a specific application example of the target-specific region. In other application examples, the target-specific region serves to hybridize to a sequence in the nucleic acid fragment to be ligated, so as to allow ligation to an end of the nucleic acid fragment to be ligated. That is, the target-specific region in the present invention is also applicable to protocols not based on sequence capture (such as whole-genome library construction). In such protocols, the target-specific region is not required to capture a specific sequence region.

Figure 2:
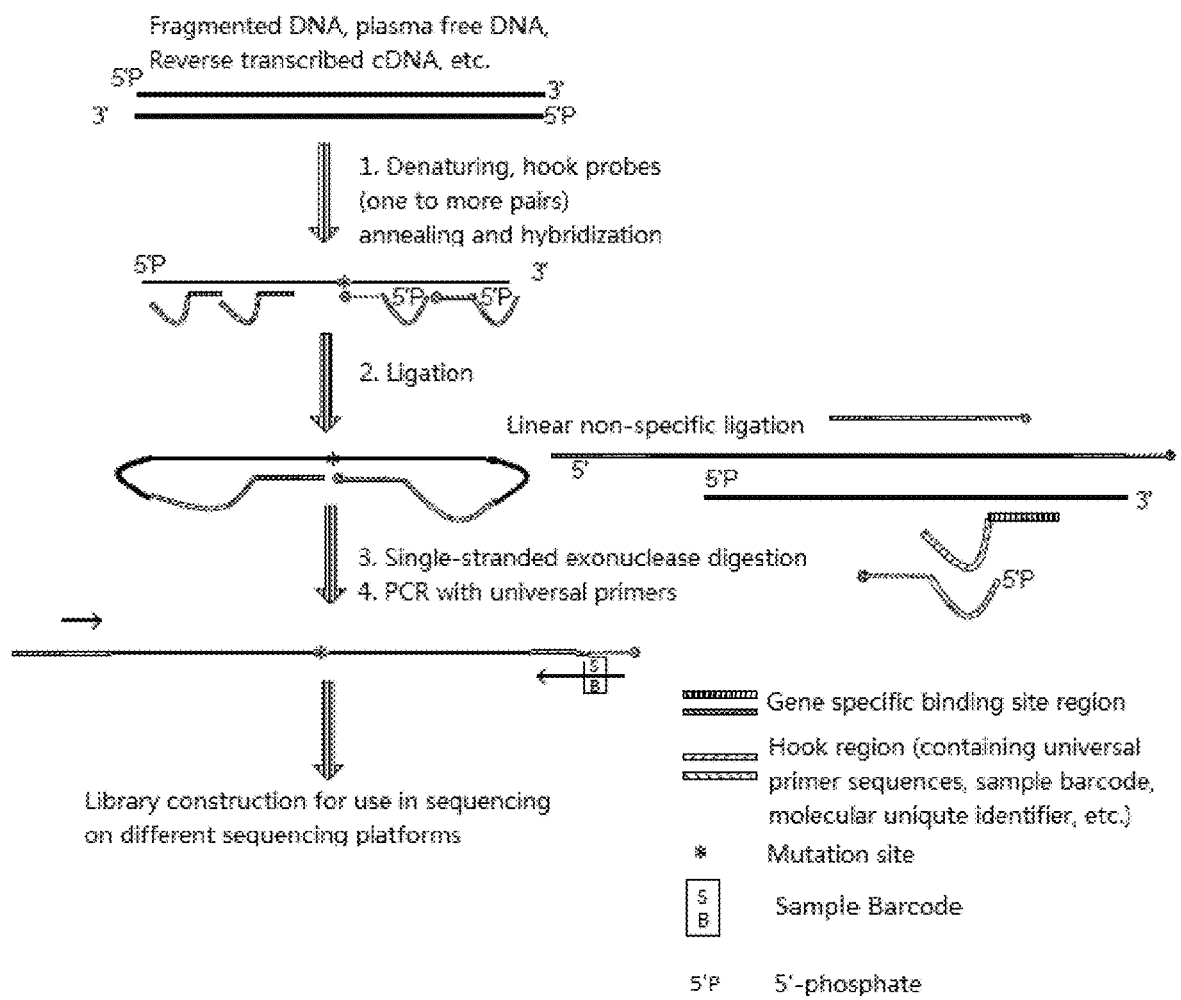
FIG. 2 shows a flow chart of a PCR protocol after bilateral hook probe hybridization and ligation.

As illustrated in FIG. 2, one or more hook probes may be designed that hybridize to the target site and/or a sequence near the target site. A combination of hook probes for capturing the same target sequence is called a hook probe set. The hook probe set may comprise one 5' hook probe and/or one 3' hook probe, or may comprise a plurality of 5' hook probes and/or a plurality of 3' hook probes. The hook probes may be designed flanking the target site and/or inside the target site, or may be designed flanking a site which is linked to the target site and/or inside a site which is linked to the target site. The so-called "target site" in the present invention may be a specific site inside the target nucleic acid (especially inside the target region in the target nucleic acid), for example, a variant site and/or gene site associated with a particular biological function (such as SNP, InDel site, gene fusion site, methylation site, etc.).

1.2 Hook Region (HR)

The hook region of the hook probe is the complete or partial nucleic acid sequence required for a template-dependent primer extension or primer-mediated PCR amplification reaction, and is also the complete or partial nucleic acid sequence of an adapter required for a sequencing reaction. It may be used for amplification, or not for amplification. The sequence of the hook region shares no homologous sequence with the template DNA (or RNA), and has no completely complementary sequence and partially complementary sequence to both the target and non-target nucleic acids. When used in NGS library construction, the universal primer binding sequence of the hook region may be selected to match the sequencing primers and/or adapter sequences of different sequencing platforms. The length of the hook region may be any suitable length and sequence, typically less than 200 nucleotides.

In various embodiments, the hook region may comprise a specific primer binding site or a universal primer binding site, a unique identifier/unique molecular identifier (UMI), a sample barcode (SB), such as a cell barcode, a sample barcode, or another barcode, and other useful elements, or any combination thereof. Each 5' hook probe and/or 3' hook probe may comprise one or more unique molecular identifiers (UMI). The position of the UMI in the hook region, and the base number and base composition of the UMI are designed according to the starting template amount and/or application purpose and/or sequencing strategy, among other purposes. Each 5' hook probe and/or 3' hook probe may comprise one sample barcode (SB). The position of the SB in the hook region, and the base number and base composition of the SB are designed according to the sample number and/or application purpose and/or sequencing strategy, among other purposes.

Figure 3:
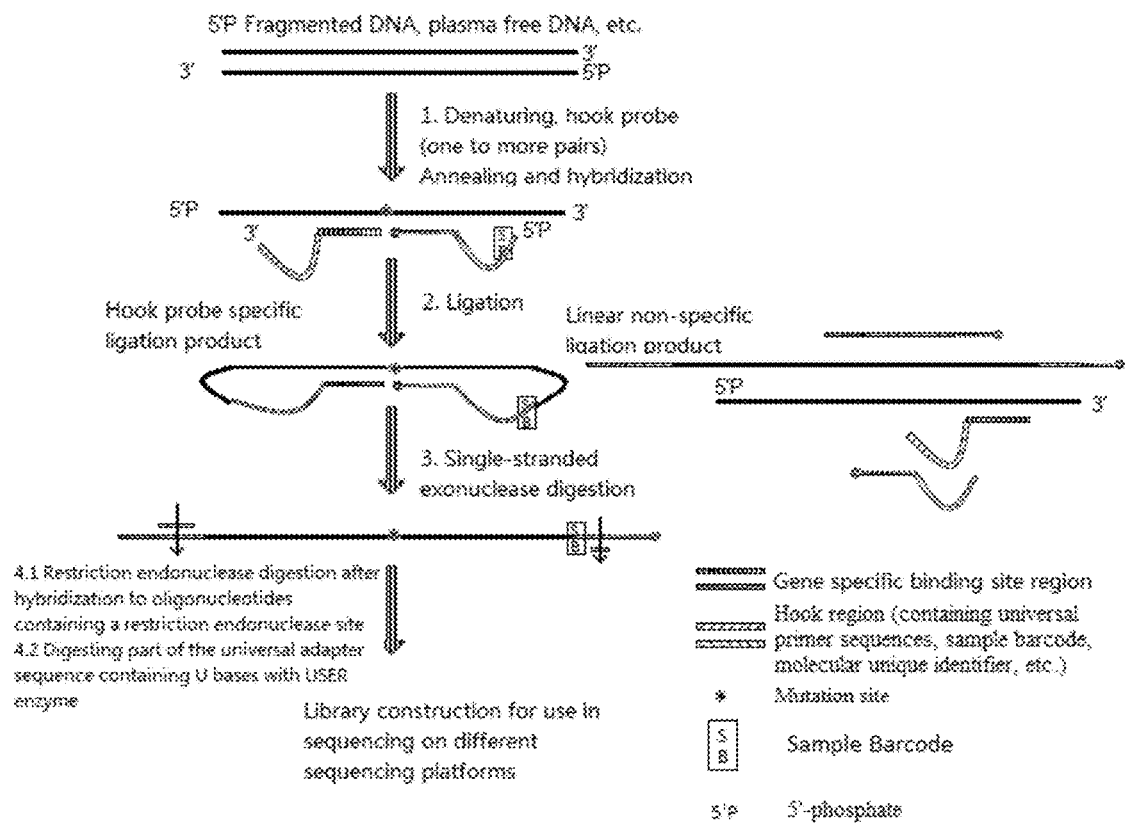
FIG. 3 shows a flow chart of a PCR-free protocol after bilateral hook probe hybridization and ligation.

In some embodiments, the hook region may comprises a restriction site, which is restriction enzyme recognition and binding site and/or one or more modified nucleotides that are cleavable, so that the hook ligation product achieves PCR free library construction and/or removal of a sequence of the TSR region (see FIG. 3). Examples of modified nucleotide/enzyme combinations include but not limited to: (i) deoxyuridine and E. coli uracil DNA glycosylase (UDG) or A. fulgidis UDG (Afu UDG) in combination with one or more enzymes that can remove an AP site, such as, human apurinic/apyrimidinic (AP) endonuclease (APE 1), endonuclease III (Endo III), endonuclease IV (Endo IV), endonuclease VIII (Endo VIII), formamidopyrimidine [fapy]-DNA glycosylase (Fpg), human 8-oxoguanine glycosylsase (hOGG1), or human Nei-like glycosylase 1 (hNEIL1) endonuclease VIII (Endo VIII); (ii) deoxyinosine and endonuclease V, or human 3-alkyladenine DNA glycosylase (hAGG) to generate an AP site and one or more enzymes that can remove an AP site, such as, APE 1, Endo III, Endo IV, Endo VIII, Fpg, hOGG1, or hNEIL1; (iii) oxidized pyrimidine nucleotide (e.g., 5,6-dihydroxythymine, thymine glycol, 5-hydroxy-5-methylhydantoin, uracil glycol, 6-hydroxy-5,6-dihydrothymine, or methyltartronylurea) and Endo VIII, Endo III, hNEIL1, or a combination thereof; (iv) oxidized purine nucleotide (e.g., 8-oxoguanine, 8-hydroxyguanine, 8-oxoadenine, fapy-guanine, methy-fapy-guanine, or fapy-adenine) and Fpg, hOGG1, hNEIL1, or a combination thereof; (v) alkylated purine (e.g., 3-mehtyladenine, 7-methylguanine, 1,N6-ethenoadenine, and hypoxanthine) and hAGG to generate an AP site and one or more enzymes that can remove an AP site, such as, APE 1, Endo III, Endo IV, Endo VIII, Fpg, hOGG1, or hNEIL1; and (vi) 5-hydroxyuracil, 5-hydroxymethyluracil, or 5-formyluracil and human single-strand-selective monofunctional uracil-DNA glycosylase SMUG1 (hSMUG1) to generate an AP site and one or more enzymes that can remove an AP site, such as, APE 1, Endo III, Endo IV, Endo VIII, Fpg, hOGG1, or hNEIL1.

1.3 Terminal Modification of the Hook Probe

The hook probe comprises a ligatable end capable of being ligated to a single-stranded end of a nucleic acid fragment (such as a target nucleic acid).

The 5' hook probe comprises a functional 3' hydroxy group capable of being ligated to the 5' end of the nucleic acid fragment (such as the target nucleic acid), and the 5' end of the 5' hook probe contains a 5' blocking group (including but not limited to 5' hydroxy group, dideoxymononucleotide, etc.) that can block the 5' hook probe from undergoing a ligation reaction with another single strand or a single strand of its own. The 3' hook probe comprises a functional 5' phosphate group capable of being ligated to the 3' end of the nucleic acid fragment (such as the target nucleic acid), and the 3' end of the 3' hook probe contains a 3' blocking group (including but not limited to 3' phosphoric acid, 3' ring-opening sugar such as 3'-phosphate-α,β-unsaturated aldehyde (PA), 3' amino modification, 3' dideoxynucleotide, 3' phosphorothioate (PS) bond or 3' phosphate, etc.) that can block the 3' hook probe from undergoing a ligation reaction with another single strand or a single strand of its own.

2. Nucleic Acid Fragment 2.1 Target Region and Target Nucleic Acid

The nucleic acid fragment to be ligated in the present invention particularly comprises a target region nucleic acid. A target region refers to a stretch or multiple stretches of contiguous nucleotide base sequence and/or one or more nucleotide bases. It may be a variant site and/or gene site associated with a particular biological function (such as SNP, InDel, SV, CNV, gene fusion, methylation site, etc.), or may be a stretch of known DNA sequence and/or RNA sequence and/or artificially synthesized nucleotide sequence, or may be one and/or more genes or a particular gene set associated with a particular function and/or a gene set of interest, or may even be a particular genome and/or transcriptome and/or a particular type of RNA (such as 16S ribosome RNA, ribozyme, antisense RNA, guide RNA, etc.).

A nucleic acid fragment comprising the target region is called a target nucleic acid in short. The target nucleic acid may be double-stranded and/or single-stranded (such as dsDNA, cfDNA, ctDNA, ssDNA, DNA/RNA hybrid, RNA, mRNA, cDNA first strand, cDNA second strand, cDNA, etc.).

2.2 Sample

A mixture formed from the target nucleic acid and fragments other than the target region is called a sample. The sample containing the target nucleic acid may be obtained from any suitable sources. For example, the sample may be obtained or provided from any organisms of interest. Such organisms include, for example, plants, animals (e.g., mammals, including humans and non-human primates); or pathogens, such as bacteria and viruses. In some cases, the sample may be, or may be obtained from, cells, tissues, secretions of a population of such organisms of interest. As another example, the sample may be a microbiome or microbiota. Optionally, the sample is an environmental sample, such as a sample of water, air, or soil.

Samples from an organism of interest, or a population of such organism of interest, can include, but not limited to, samples of bodily fluids (including, but not limited to, blood, urine, serum, lymph, saliva, anal and vaginal secretions, perspiration and semen), cells, tissues, biopsies, research samples (e.g., products of nucleic acid amplification reactions, such as PCR amplification reactions); purified samples (such as purified genomic DNA, RNA etc.), and raw samples (such as bacteria, virus, genomic DNA, etc.). Methods of obtaining target polynucleotides (e.g., genomic DNA, total RNA, etc.) from organisms are well known in the art.

2.3 Fragmentation

Except those samples of natural fragmentation (e.g., cfDNA, ctDNA, a stretch of synthesized nucleic acid, etc.), the samples in most embodiments (e.g., genomic DNA, etc.) need fragmentation processing to produce fragments of one or more specific sizes or to produce a population of fragments having a narrow distribution of fragment lengths. Any methods of fragmentation can be used. For example, fragmentation can be accomplished by physical means (e.g., ultrasonic cleavage, acoustic shearing, needle shearing, nebulization, or sonication), or by chemical methods (e.g., heat and divalent metal cation), or by enzymatic methods (e.g., using endonucleases, nickases, or transposases). Methods of fragmentation are known in the art, see e.g., US 2012/0004126.

2.4 Size Selection of Nucleic Acid Fragments

Depending on different embodiments, for fragmented samples, target nucleic acids or nucleic acid fragments (e.g., fragmented genomic DNA or RNA) need to be subjected to a size selection step to obtain nucleic acid fragments having a certain fragment size or size range. Any methods of size selection may be used. For example, in some embodiments, fragmented target nucleic acids may be separated by gel electrophoresis and the band or region corresponding to a particular fragment size or size range is extracted and purified from the gel. In some embodiments, a purification column may be used to select for fragments having a particular minimum size. In some embodiments, paramagnetic beads may be used to selectively bind DNA fragments having a desired size range. In some embodiments, the solid-phase reversible immobilization (SPRI) method may be used to enrich for nucleic acid fragments having a particular size or size range. In some embodiments, a combination of the size selection methods described above may be used.

Fragmented nucleic acids are selected that are in a size range of about 50 to about 3000 bases. Fragments in such a range may be fragments of a particular size, or may be fragments of a particular average size, or may be fragments of a particular range.

3. Ligase

The formation of a hook probe ligation product requires the use of the hook probe in combination with one or more ligases. The ligase used in the present invention is capable of intermolecular ligation of polynucleotides with single-stranded ends under appropriate conditions and at appropriate substrate concentrations.

In some embodiments, the ligase is a "single-stranded DNA or RNA ligase". As used herein, Cirligase can catalyze the formation of a covalent phosphodiester bond between two different nucleic acid strands under suitable reaction conditions. For example, the ligase catalyzes the synthesis of a phosphodiester bond between the 3'-hydroxy group of a first polynucleotide and the 5'-phosphoryl group of a second polynucleotide. In some cases, hybridization of the hook probe to the target nucleic acid can produce a substrate for ligation. For example, hybridization of the 5' hook probe to the target nucleic acid can produce a 3'-hydroxy group suitable for ligation to the 5' end of the target nucleic acid. Optionally, the 5' hook probe comprises a blocked 5' end that is not suitable for ligation. Similarly, hybridization of the 3' hook probe to the target nucleic acid can produce a free 5' phosphate that can be ligated to the 3' end of the target nucleic acid. Optionally, the 3' hook probe comprises a blocked 3' end that is not suitable for ligation.

In some embodiments, the ligase is a thermostable RNA ligase, including but not limited to TS2126 RNA ligase or an adenylated form of TS2126 RNA ligase, CIRCLIGASE™ ssDNA ligase or CIRCLIGASE II™ ssDNA ligase (see Epicentre Biotechnologies, Madison, Wis.; Lucks et al., 2011, Proc. Natl. Acad. Sci. USA 108:11063-11068; Li et al., 2006, Anal. Biochem. 349:242-246; Blondal et al., 2005, Nucleic Acids Res. 33: 135-142), thermoautotrophicum RNA ligase 1 or "MthRn1 ligase" (see U.S. Pat. Nos. 7,303,901, 9,217,167, and International Publication No. WO2010/094040), T4 DNA ligase (e.g., T4 RNA ligase I; Zhang et al., 1996, Nucleic Acids Res. 24:990-991; Tessier et al., 1986, Anal. Biochem. 158:171-178), and thermostable 5'ApA/DNA ligase.

On the basis of the hook probe of the present invention, the present invention also provides a kit, which comprises the hook probe of the present invention, and optionally, further comprises at least one ligase. The ligase is used for ligating a ligatable end of the hook probe to an end of the nucleic acid fragment to be ligated, and may be any of the ligases described above.

On the basis of the hook probe of the present invention, the present invention also provides a use of the hook probe of the present invention in the construction of a nucleic acid sequencing library, especially a high throughput sequencing library. It is to be appreciated that the hook probe of the present invention finds very wide application and is not limited to nucleic acid sequencing library construction, with just a main use thereof being presented herein.

On the basis of the hook probe of the present invention, the present invention also provides a nucleic acid ligation method, comprising:

annealing and hybridizing the hook probe of the present invention to a denatured nucleic acid fragment to be ligated; and ligating a ligatable end of the hook probe to a single-stranded end of the nucleic acid fragment in the presence of a ligase.

It is to be appreciated that the nucleic acid ligation method of the present invention is a fundamental method. There is no specific limitation on the application of the method, and it can be used in any application scenarios in which ligation of the hook probe of the present invention to a nucleic acid fragment is required. One typical but not limiting application scenario is the use in nucleic acid sequencing library construction, as specifically described below.

On the basis of the hook probe of the present invention, the present invention also provides a method for nucleic acid sequencing library construction, comprising:

a step of annealing and hybridizing the hook probe of the present invention to a denatured nucleic acid fragment to be ligated; and a step of ligating a ligatable end of the hook probe to a single-stranded end of the nucleic acid fragment in the presence of a ligase.

In order to eliminate the influence of undesired nucleic acids on subsequent reactions, the method for nucleic acid sequencing library construction may also comprise:

a step of removing linear non-specific ligation products, excess nucleic acid fragments and excess hook probes; preferably, digesting the linear non-specific ligation products, excess nucleic acid fragments and excess hook probes using a single-stranded exonuclease.

The product obtained after ligase ligation and/or the product obtained after removal of undesired nucleic acids may take two alternative paths during subsequent process of nucleic acid sequencing library construction, that is, PCR amplification path and PCR free path.

With regard to the PCR amplification path, the above-described method further comprises:

a step of subjecting the ligation product of the hook probe and the nucleic acid fragment to PCR amplification using universal primers.

With regard to the PCR-free path, the hook region may comprise a restriction enzyme binding site cleavable with a restriction enzyme and/or one or more modified nucleotides that are cleavable, and the method described above further comprises:

a step of subjecting the restriction enzyme binding site to restriction enzyme cleavage using a restriction enzyme and/or cleaving the one or more modified nucleotides using a cleaving enzyme.

On the basis of the above fundamental principle and element design, the present invention proposes a series of methods for constructing nucleic acid sequencing libraries. These methods can be applied to different sequencing platforms. Each specific library construction protocol will be described in detail below. It is noted that besides the embodiments described below, other similar protocols and variants thereof are also included within the claimed scope of the present invention.

The protocols for bilateral hook probe hybridization are as shown in FIG. 2 and FIG. 3. A nucleic acid fragment (such as a target nucleic acid) is captured and hybridized by the 5' hook probe and the 3' hook probe partially matching the 5' end and 3' end of the nucleic acid fragment respectively. After intermolecular ligation of the resulting hybridization complex is complete, a specific double hook ligation product is formed. PCR amplification (see FIG. 2) or PCR-free library construction (see FIG. 3) of the ligation product is achieved by virtue of the hook region. When the GSP region is a stretch of specific target nucleic acid hybridization sequence, this protocol can be used in the target sequence capture and library construction procedure, or can be used for rapid detection of unknown sequences flanking both ends of a known sequence (for example, rapid-amplification of cDNA ends (RACE) by PCR) or artificial sequence joining in synthetic biology. When the GSP region is a stretch of random sequence, this protocol can be used in PCR library construction or PCR-free library construction of genomic DNA or RNA.

In an embodiment, the hook probe includes the 5' hook probe and the 3' hook probe. The 3' end of the hook region of the 5' hook probe has a functional 3' hydroxy group capable of being ligated to the 5' end of the nucleic acid fragment; and the 5' end of the hook region of the 3' hook probe has a functional 5' phosphate group capable of being ligated to the 3' end of the nucleic acid fragment; and the hook region of the 5' hook probe and the hook region of the 3' hook probe respectively comprise a universal primer binding site. As shown in FIG. 2, the method for nucleic acid sequencing library construction in the embodiment specifically comprises the following steps: (1) annealing and hybridizing the hook probes (such as one or more pairs) to a denatured nucleic acid fragment to be ligated (such as fragmented DNA, circulating free DNA or reverse transcribed cDNA, etc.); (2) in the presence of a ligase, ligating the functional 3'-hydroxy group of the 5' hook probe to the 5' end of the nucleic acid fragment, and ligating the functional 5'-phosphate group of the 3' hook probe to the 3' end of the nucleic acid fragment; (3) digesting the linear non-specific ligation products, excess nucleic acid fragments and excess hook probes using a single-stranded exonuclease; and (4) subjecting the ligation product of the hook probes and the nucleic acid fragment to PCR amplification using universal primers that match the hook region sequences, wherein the universal primers are respectively complementary to the universal primer binding sites of the 5' hook probe and the 3' hook probe, and the primers may contain a sample barcode. The products obtained by amplification are target nucleic acid molecules with sequencing adapter sequences attached on both ends, and can be use in subsequent library construction and sequencing.

In another embodiment, the hook probe includes the 5' hook probe and the 3' hook probe. The 3' end of the hook region of the 5' hook probe has a functional 3' hydroxy group capable of being ligated to the 5' end of the nucleic acid fragment; and the 5' end of the hook region of the 3' hook probe has a functional 5' phosphate group capable of being ligated to the 3' end of the nucleic acid fragment; and the hook region of the 5' hook probe and the hook region of the 3' hook probe respectively comprise a restriction enzyme binding site cleavable with a restriction enzyme and/or one or more modified nucleotides that are cleavable. As shown in FIG. 3, the method for nucleic acid sequencing library construction in the embodiment specifically comprises the following steps: (1) annealing and hybridizing the hook probes (such as one or more pairs) to a denatured nucleic acid fragment to be ligated (such as fragmented DNA, circulating free DNA or reverse transcribed cDNA, etc.); (2) in the presence of a ligase, ligating the functional 3'-hydroxy group of the 5' hook probe to the 5' end of the nucleic acid fragment, and ligating the functional 5'-phosphate group of the 3' hook probe to the 3' end of the nucleic acid fragment; (3) digesting the linear non-specific ligation products, excess nucleic acid fragments and excess hook probes using a single-stranded exonuclease; and (4) any one or both of the following two alternatives: 4.1. when the hook region sequence contains a restriction endonuclease recognition sequence, denaturing the ligation product followed by hybridization to the complementary sequence of the restriction endonuclease recognition sequence to form a restriction endonuclease recognition site, and cleaving with a corresponding restriction endonuclease to remove unnecessary sequences (such as the GSP region and/or the hook region sequence irrelevant to sequencing) on the hook probe; and 4.2. when the hook region sequence contains a U base, cleaning with USER enzyme to remove unnecessary sequences (such as the GSP region and/or the hook region sequence irrelevant to sequencing) on the hook probe, and the fragments obtained after the removal can be used in subsequent library construction and sequencing.

The protocols for monolateral hook probe hybridization is as shown in FIG. 4 to FIG. 7. A nucleic acid fragment (such as a target nucleic acid) is captured and hybridized by the 5' hook probe or the 3' hook probe partially matching the 5' end or 3' end of the nucleic acid fragment. After intermolecular ligation of the resulting hybridization complex is complete, a specific single hook ligation product is formed. Then primer extension and branch ligation, among other techniques, are employed to achieve PCR or PCR-free enrichment and detection of the nucleic acid fragment. Likewise, the protocols for monolateral hook probe hybridization are also applicable to target sequence capture and library construction procedure (especially gene fusion and SV detection), whole-genome library construction procedure, RNA-seq library construction procedure, RACE, sequence artificial joining, etc.

Figure 4:
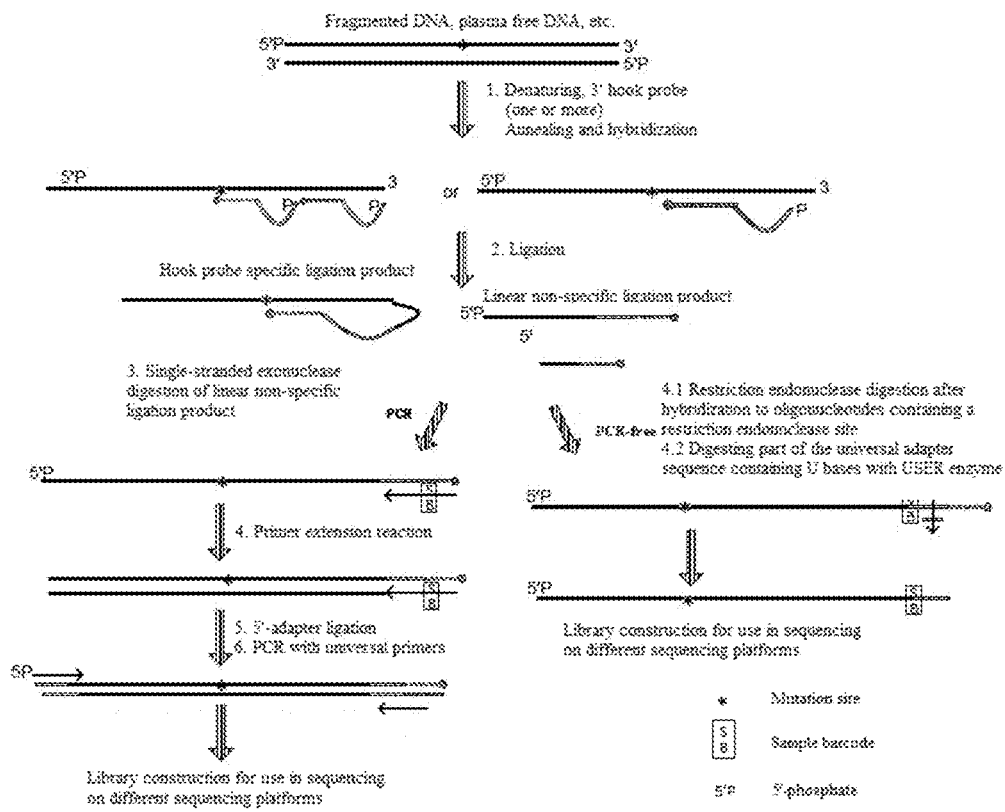
FIG. 4 shows a flow chart of a PCR/PCR-free protocol after monolateral 3' hook probe hybridization and ligation.

In an embodiment, the hook probe includes the 3' hook probe. The 5' end of the hook region of the 3' hook probe has a functional 5'-phosphate group capable of being ligated to the 3'-end of the nucleic acid fragment. As shown in FIG. 4, the method for nucleic acid sequencing library construction in the embodiment specifically comprises the following steps: (1) annealing and hybridizing the hook probe (one or more) to a denatured nucleic acid fragment to be ligated (such as fragmented DNA, circulating free DNA or reverse transcribed cDNA, etc.); (2) in the presence of a ligase, ligating the functional 5'-phosphate group of the 3' hook probe to the 3' end of the nucleic acid fragment; (3) digesting the linear non-specific ligation products, excess nucleic acid fragments and excess hook probes using a single-stranded exonuclease; (4) performing a primer extension reaction using primer sequences completely or partly complementary to the hook region sequence of the 3' hook probe, for use in a PCR library construction protocol; (5) connecting a 5'-adapter (such as a 5' blunt end adapter or a T-A linking adapter) to the 5'-end of the product of the extension reaction; and (6) performing PCR amplification using primer sequences completely or partly complementary to the 5' adapter and the hook region sequence of the 3' hook probe, the amplification product being for in subsequent library construction and sequencing.

In another embodiment, the hook probe includes the 3' hook probe. The 5' end of the hook region of the 3' hook probe has a functional 5'-phosphate group capable of being ligated to the 3'-end of the nucleic acid fragment; and the hook region of the 3' hook probe comprises a restriction enzyme binding site cleavable with a restriction enzyme and/or one or more modified nucleotides that are cleavable. As shown in FIG. 4, the method for nucleic acid sequencing library construction in the embodiment specifically comprises the following steps: (1) annealing and hybridizing the hook probe (one or more) to a denatured nucleic acid fragment to be ligated (such as fragmented DNA, circulating free DNA or reverse transcribed cDNA, etc.); (2) in the presence of a ligase, ligating the functional 5'-phosphate group of the 3' hook probe to the 3' end of the nucleic acid fragment; (3) digesting the linear non-specific ligation products, excess nucleic acid fragments and excess hook probes using a single-stranded exonuclease; and (4) achieving a PCR-free protocol by any one or both of the following two alternatives: 4.1. when the hook region sequence contains a restriction endonuclease recognition sequence, denaturing the ligation product followed by hybridization to the complementary sequence of the restriction endonuclease recognition sequence to form a restriction endonuclease recognition site, and cleaving with a corresponding restriction endonuclease to remove unnecessary sequences (such as the GSP region and/or the hook region sequence irrelevant to sequencing) on the hook probe; and 4.2. when the hook region sequence contains a U base, cleaning with USER enzyme to remove unnecessary sequences (such as the GSP region and/or the hook region sequence irrelevant to sequencing) on the hook probe, and the fragments obtained after the removal can be used in subsequent library construction and sequencing.

Figure 5:
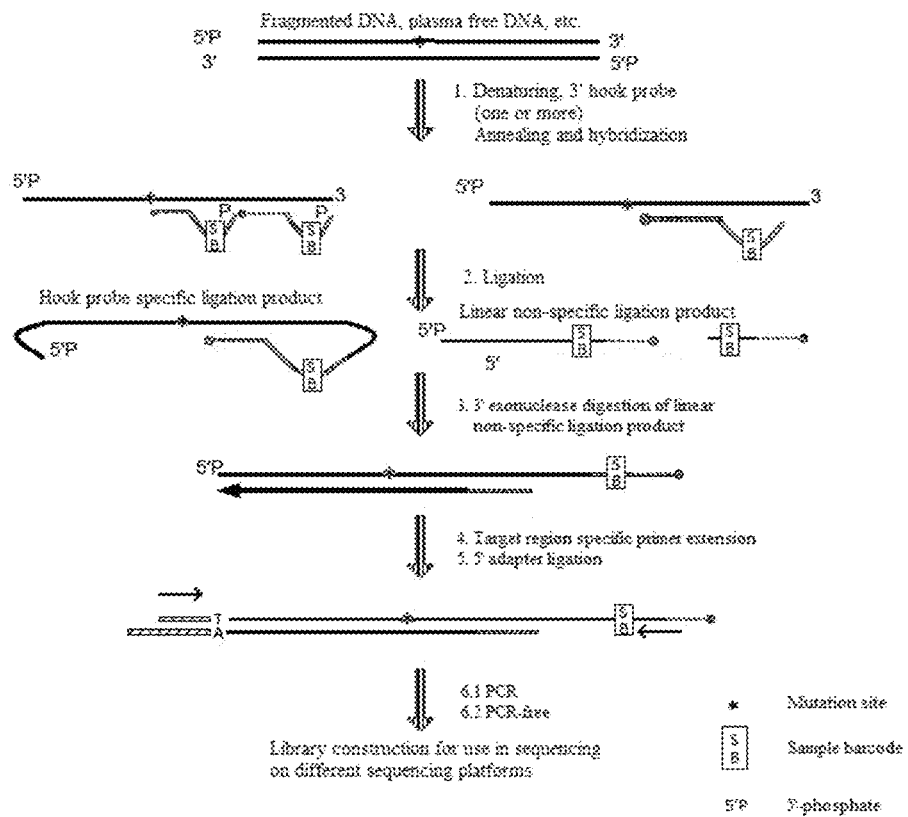
FIG. 5 shows a flow chart of another PCR/PCR-free protocol after monolateral 3' hook probe hybridization and ligation.

In another embodiment, the hook probe includes the 3' hook probe. The 5' end of the hook region of the 3' hook probe has a functional 5'-phosphate group capable of being ligated to the 3'-end of the nucleic acid fragment; and the nucleic acid fragment comprises a target region sequence. As shown in FIG. 5, the method for nucleic acid sequencing library construction in the embodiment specifically comprises the following steps: (1) annealing and hybridizing the hook probe (one or more) to a denatured nucleic acid fragment to be ligated (such as fragmented DNA, circulating free DNA or reverse transcribed cDNA, etc.); (2) in the presence of a ligase, ligating the functional 5'-phosphate group of the 3' hook probe to the 3' end of the nucleic acid fragment; (3) digesting the linear non-specific ligation products, excess nucleic acid fragments and excess hook probes using a single-stranded exonuclease; (4) performing a primer extension reaction using primer sequences completely or partly complementary to the target region sequence or an adjacent region thereof; (5) connecting a 5'-adapter (such as a 5' blunt end adapter or a T-A linking adapter) to the 5'-end of the product of the extension reaction; and (6) performing PCR amplification using primer sequences completely or partly complementary to the 5' adapter and the hook region sequence of the 3' hook probe, the amplification product being for use in subsequent library construction and sequencing. PCR-free library construction can also be performed usign a method similar to that in FIG. 4.

Figure 6:
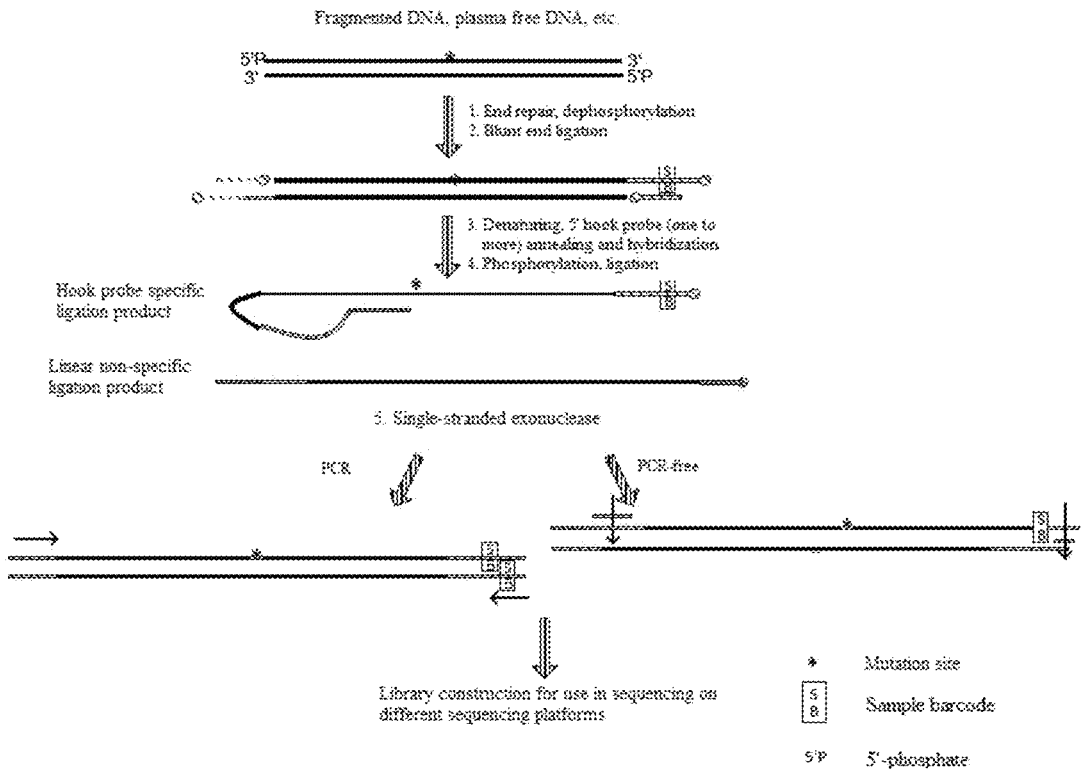
FIG. 6 shows a flow chart of a PCR/PCR-free protocol after monolateral 5' hook probe hybridization and ligation.

In another embodiment, the hook probe includes the 5' hook probe. The 3' end of the hook region of the 5' hook probe has a functional 3'-hydroxy group capable of being ligated to the 5'-end of the nucleic acid fragment; and the hook region of the 5' hook probe comprises a universal primer binding site. As shown in FIG. 6, the method for nucleic acid sequencing library construction in the embodiment specifically comprises the following steps: (1) subjecting the nucleic acid fragment to be ligated (such as fragmented DNA or circulating free DNA) to end repair and dephosphorylation treatment; (2) connecting a 3'-adapter (such as a blunt end adapter) to the 3'-end of the end-repaired and dephosphorylated nucleic acid fragment, the 3' adapter having a universal primer binding site; (3) annealing and hybridizing the hook probe (such as one or more) to the nucleic acid fragment having connected with the 3' adapter; (4) after phosphorylation treatment, in the presence of a ligase, ligating the functional 5'-phosphate group of the 3' hook probe to the 3' end of the nucleic acid fragment; (5) digesting the linear non-specific ligation products, excess nucleic acid fragments and excess hook probes using a single-stranded exonuclease; and (6) performing PCR amplification on the ligation product of the hook probe and the nucleic acid fragment using universal primers, wherein the universal primers are complementary to the universal primer binding sites of the 5' hook probe and the 3' adapter respectively.

In another embodiment, the hook probe includes the 5' hook probe. The 3' end of the hook region of the 5' hook probe has a functional 3'-hydroxy group capable of being ligated to the 5'-end of the nucleic acid fragment; and the hook region of the 5' hook probe comprises a restriction enzyme binding site cleavable with a restriction enzyme and/or one or more modified nucleotides that are cleavable. As shown in FIG. 6, the method for nucleic acid sequencing library construction in the embodiment specifically comprises the following steps: (1) subjecting the nucleic acid fragment to be ligated (such as fragmented DNA or circulating free DNA) to end repair and dephosphorylation treatment; (2) connecting a 3'-adapter (such as a blunt end adapter) to the 3'-end of the end-repaired and dephosphorylated nucleic acid fragment, the 3' adapter having a universal primer binding site; (3) annealing and hybridizing the hook probe (such as one or more) to the denatured nucleic acid fragment having connected with the 3' adapter and having been denatured; (4) after phosphorylation treatment, in the presence of a ligase, ligating the functional 5'-phosphate group of the 3' hook probe to the 3' end of the nucleic acid fragment; (5) digesting the linear non-specific ligation products, excess nucleic acid fragments and excess hook probes using a single-stranded exonuclease; and (6) subjecting the restriction enzyme binding site to restriction enzyme cleavage using a restriction enzyme and/or cleaving the one or more modified nucleotides using a cleaving enzyme, achieving a PCR-free library construction protocol.

Figure 7:
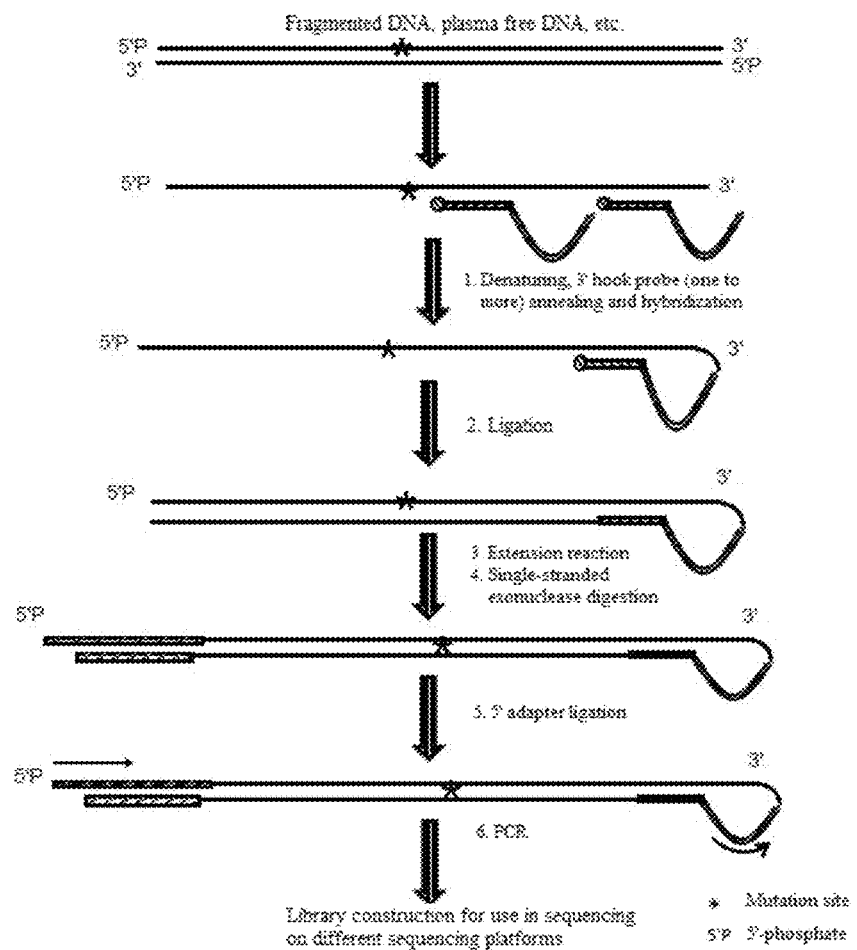
FIG. 7 shows a flow chart of a PCR protocol after monolateral 3' hook probe hybridization and ligation.

In another embodiment, the hook probe includes the 3' hook probe. The 5' end of the hook region of the 3' hook probe has a functional 5'-phosphate group capable of being ligated to the 3'-end of the nucleic acid fragment. As shown in FIG. 7, the method for nucleic acid sequencing library construction in the embodiment specifically comprises the following steps: (1) annealing and hybridizing the hook probe (such as one or more) to a denatured nucleic acid fragment to be ligated (such as fragmented DNA or circulating free DNA); (2) in the presence of a ligase, ligating the functional 5'-phosphate group of the 3' hook probe to the 3' end of the nucleic acid fragment; (3) in the presence of a polymerase, performing an extension reaction with the 3' end of the 3' hook probe as the reaction start point for the polymerase; (4) digesting the linear non-specific ligation products, excess nucleic acid fragments and excess hook probes using a single-stranded exonuclease; (5) connecting a 5'-adapter (5' blunt end adapter or a T-A linking adapter) to the 5'-end of the product of the extension reaction; and (6) performing PCR amplification using primer sequences completely or partly complementary to the 5' adapter and the hook region sequence of the 3' hook probe, the amplification product being for use in subsequent library construction and sequencing.

The method for nucleic acid sequencing library construction of the present invention, as an improved method for rapid target region enrichment, solves the problems of cumbersome procedure, time-consuming process and high cost of library construction associated with existing liquid phase probe hybridization and capture techniques. Also, the method of the present invention is suitable for various types of samples, including but not limited to whole genomic DNA, cfDNA, ctDNA, FFPE DNA, RNA, mRNA, etc., and can detect various types of genetic variations, such as SNP (single nucleotide polymorphism), InDel (insertion-deletion), CNV (copy number variations), SV (structural variation), and gene fusion. Variant embodiments of the present invention can also be used for rapid and direct library construction of whole-genomic DNA, cfDNA, ctDNA, and FFPE DNA, etc.

With ingenious design of the hook probe and cooperation of a ligase, the present invention achieves rapid hybridization and capture of a nucleic acid fragment (such as a target sequence) and addition of a stretch of known tool sequence at the same time, and by ingeniously designing and using the known tool sequence to perform subsequent operations and reactions, the present invention can accomplish different applications. In particular, the present invention can be suitable for a wide range of sample types, detection types and application fields (not limited to high throughput library construction, but can also be used in molecular cloning and synthetic biology, among other fields). It is anticipated that the realization of the present invention will greatly result in process simplification, time reduction and cost saving, will break through the limitations of applicable sample types, will benefit a variety of scientific research applications and kit packages, and will have very promising market potential and prospect.

The technical solutions and effects of the present invention will be described in detail by way of Experimental examples and Examples below. It is appreciated that the Experimental examples and the Examples are only exemplary of the present invention and shall not be construed as limiting the scope of protection of the present invention.

The Experimental example 1 and Experimental example 2 below demonstrated the fundamental principle of the present invention. That is, under suitable reaction conditions, a nucleic acid fragment, such as a target region nucleic acid single-stranded fragment (containing a phosphate group at the 5' end or a hydroxy group at the 3' end), and a target-specific hook probe (containing a phosphate group at the 5' end or a hydroxy group at the 3' end) with part of the sequence thereof being complementary to the target region nucleic acid single-stranded fragment, will form a hybridization complex. Under the catalysis of a certain ligase, the intermolecular single strand ligation product of the non-complementary regions (the 5' end of the target region nucleic acid single strand and the 3' end of the hook probe) of the hybridization complex is produced in a higher proportion than the intramolecular single strand circularization product of the target region nucleic acid single-stranded fragment, and the single strand intermolecular product formed between the single strands without complementary regions occurs in a very low proportion.

Experimental Example 1

Figure 10:
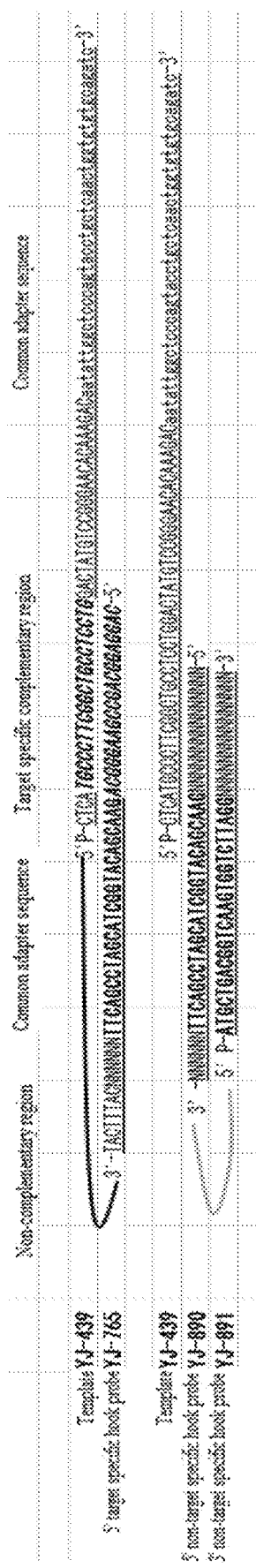
FIG. 10 shows a schematic diagram of sequence ligation in an Experimental Example verifying the fundamental principle, in which template YJ-439 (SEQ ID NO: 1), 5' target specific hook probe YJ-890 (SEQ ID NO: 2), 5' non-target specific hook probe YJ-890 (SEQ ID NO: 3) and 3' non-target specific hook probe YJ-891 (SEQ ID NO: 4) are shown.

This experimental example studied the incubation reaction of the target region nucleic acid single-stranded fragment (YJ-439) and the target-specific 5' hook probe (YJ-765) (FIG. 10) in the presence of Cirligase I (Epicenter) at different reaction temperatures.

Figure 8:
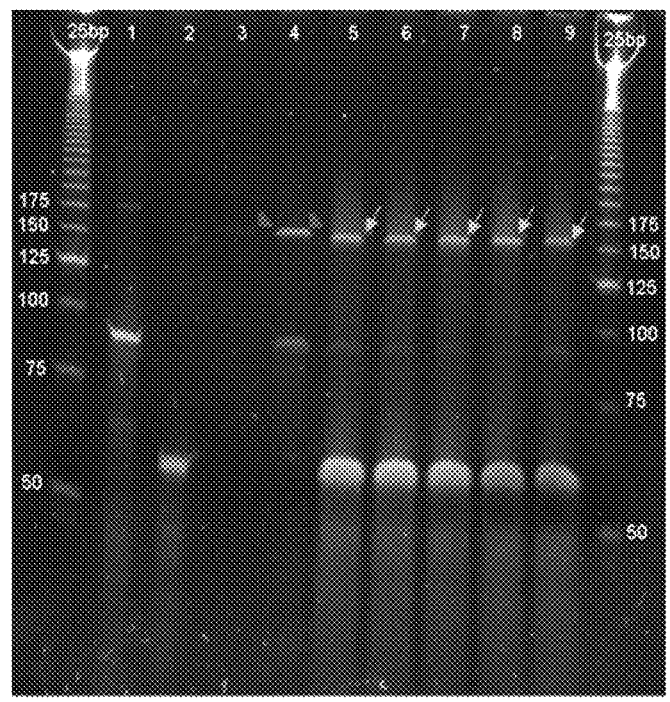
FIG. 8 shows the 10% denatured polyacrylamide gel (U-PAGE) image of the reaction product obtained from incubation of the target region nucleic acid single-stranded fragment (YJ-439) and the target-specific 5' hook probe (YJ-765) in the presence of Cirligase I at different reaction temperatures.

FIG. 8 shows a 10% denatured polyacrylamide gel (U-PAGE) image of the product. The results show that:

Lane 1: target region nucleic acid single-stranded fragment YJ-439 (synthesized by IDT, 90 nt), the sequence being as follows:

(SEQ ID NO: 1)
P-CTCATGCCCTTCGGCTGCCTCCTGGACTATGTCCGGGAACACAAAGA

Caatattggctcccagtacctgctcaactggtgtgtgcagatc.

Lane 2: target-specific 5' hook probe YJ-765 (synthesized by IDT, 59 nt, containing a 20 nt sequence complementary to YJ-439), the sequence being as follows:

(SEQ ID NO: 2)
CAGGAGGCAGCCGAAGGGCAGAACGACATGGCTACGATCCGACTTNNNN

NNCATTTCAT.

Lane 3: the product resulting from exonucleases I and III treatment after the reaction of YJ-439 in the presence of Cirligase I at an optimum temperature of 55° C.

Lane 4: the product after the reaction of YJ-439 in the presence of Cirligase I at an optimum temperature of 55° C.

Lanes 5-9: The products after the reaction of YJ-439/YJ-765 in the presence of Cirligase I at different temperatures (25° C., 37° C., 45° C., 55° C., and 60° C.).

Lane 3 (with exonuclease I and III treatment) and lane 4 (without exonuclease I and III treatment) indicate that YJ-439 formed a single-stranded loop itself (at about 150 nt, marked with a triangle) in the presence of Cirligase I at an optimal temperature of 55° C. As shown in lanes 5-9, when incubated with the hook probe (YJ-765) at different temperatures (25° C., 37° C., 45° C., 55° C., and 60° C.), most of the YJ-439 formed ligation products with the hook probe (149 nt, marked with arrows) rather than forming single-stranded loops, and these products can be degraded by exonucleases I and III.

Experimental Example 2

This experimental example studied the incubation reaction of the target region nucleic acid single-stranded fragment (YJ-439) and the non-target-specific 5' hook probe (YJ-890) and the non-target-specific 3' hook probe (YJ-891) (FIG. 10) in the presence of Cirligase I (Epicenter) at different reaction temperatures.

Figure 9:
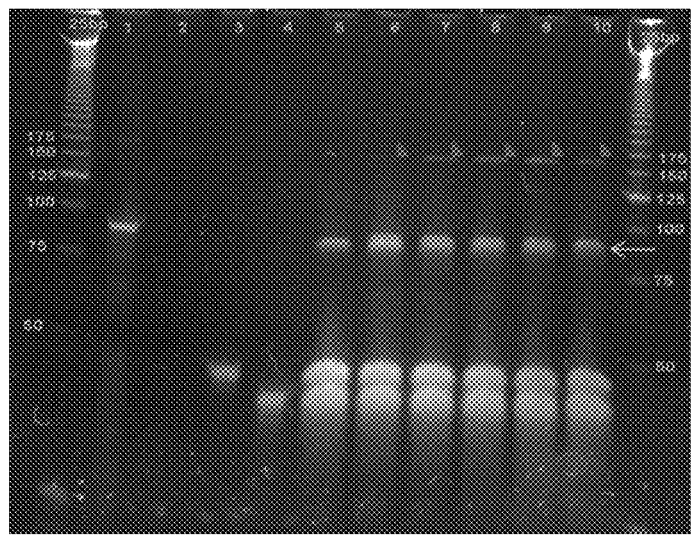
FIG. 9 shows the 10% U-PAGE image of the reaction product obtained from incubation of the target region nucleic acid single-stranded fragment (YJ-439) and the non-target-specific 5' hook probe (YJ-890) and the non-target-specific 3' hook probe (YJ-891) in the presence of Cirligase I at different reaction temperatures.

FIG. 9 shows a 10% U-PAGE gel image of the product. The results show that:

Lane 1: target region nucleic acid single-stranded fragment YJ-439 (synthesized by IDT, 90 nt).

Lane 2: the product resulting from exonucleases I and III treatment after the reaction of YJ-439 in the presence of Cirligase I at an optimum temperature of 55° C.

Lane 3: non-target-specific 5' hook probe YJ-890 (synthesized by IDT, 46 nt), the sequence of which being that obtained by substituting a random base sequence for the 20 bp sequence in YJ-765 which is complementary to YJ-439:

(SEQ ID NO: 3)
NNNNNNNNNNNNNNNNNNNNGAACGACATGGCTACGATCCGACTTNNNNNN

Lane 4: non-target-specific 3' hook probe YJ-891 (synthesized by IDT, 40 nt), the sequence being:

(SEQ ID NO: 4)
P-NNNNNNNNNNNNNNNNNNNNGAACGACATGGCTACGATCCGACTTNNNN
NN-P.

Lane 5: the product after the reaction of YJ-890/YJ-891 in the presence of Cirligase I at an optimum temperature of 55° C.

Lanes 6-10: the product after the reaction of YJ-439/YJ-890/YJ-891 in the presence of Cirligase I at different temperatures (25° C., 37° C., 45° C., 55° C., and 60° C.).

Lane 2 (with exonucleases I and III treatment) shows that YJ-439 formed a single-stranded loop itself in the presence of Cirligase I at an optimal temperature of 55° C. (about 150 nt, marked with a triangle). Lane 5 shows that the non-target-specific hook probes YJ890 and YJ-891 formed an intermolecular ligation product (86 nt, marked with the long arrows for lanes 5-10) in the presence of Cirligase I at the optimum temperature of 55° C. When incubated with the non-target-specific hook probes (YJ-890/YJ-891) at different temperatures (25° C., 37° C., 45° C., 55° C., and 60° C.) shown in lanes 6-10, most of the ligaton products were a single-stranded loop (about 150 nt, marked with a triangle), which was not easily processed by an exonuclease (data not shown), and an intermolecular ligation product (86 nt, marked with the long arrows for lanes 5-10) formed by the 5' hook probe and the 3' hook probe, which can be degraded by exonucleases I and III (data not shown), while the random intermolecular ligation products (136 nt and/or 130 nt) between the template (YJ-439) and the non-target specific hook probe (YJ890 and YJ-891) were barely seen. Therefore, comparing with the results in FIG. 8, it is speculated that after a partial sequence hybridization reaction between the template (YJ-439) and the target-specific hook probe (YJ-765) to form a template 5' single strand and a target specific probe 3' single strand that are close in distance, the chance of intermolecular ligation reaction between the template and the probe be significantly increased.

Example 1: Bilateral Hook Probe Hybridization Test

1. Sample Collection and Processing

Fragmentase was used to fragment the human NA12878 (GM12878, CORIELL INSTITUTE) genomic DNA, and then DNA fragments of 200-400 bp were selected using the double selection method.

2. Denaturing and Hybridization

Preparation of the hybridization reaction system: for each reaction, 20 ng of fragmented human NA12878 (GM12878, CORIELL INSTITUTE) genomic DNA were mixed with 2 μl of the 3' hook probe at a respective concentration (0.1 μM, 0.01 μM, or 0.005 μM), 1 μL of the reaction buffer was added, and then water was added to make up to 10 μL. The mixture was vortexed well and allowed to react in a PCR instrument in the following procedure: 95° C., 5 min, cooling to 42° C. at a rate of 0.1 sec, 42° C. reaction for 1 h, and storage at 42° C. The 3' hook probe was designed as follows:
/5phos/ATGCTGACGGTCAAGTGGTCTTAGGNNNNNNNNNNNNNNNNN/3AmMO/ (SEQ ID NO: 5, the sequence underlined is partial adapter reverse complementary sequence, and the sequence not underlined is the hybridization complementary sequence designed for different ROI regions).

Some probe sequences are shown in Table 1 below.

TABLE 1

| ROI site | Position | Primer name | Primer sequence |
| --- | --- | --- | --- |
| > Fusion_chr10_61638615_chr10_43609947_CCDC6_-_RET_+ | DownstreamAA-239 | Fusion_CCDC6/RET_1_Hook2 | /5phos/ATGCTGACGGTCAAGTGGTCTTAGGAGGACAGCGGCTGCGATCAC/3AmMO/ (SEQ ID NO: 6) |
| InDel_chr4_55592185_KIT_+_c.1509_1510insGCCTAT_101 | DownstreamAA-247 | InDel_KIT_1_Hook2 | /5phos/ATGCTGACGGTCAAGTGGTCTTAGGTATACCTTTGTTGTTACCTTTAAATGCAAAGTTAA/3AmMO/ (SEQ ID NO: 7) |
| SNV_chr10_43617416_RET_+_c.2753T>C_101_1 | DownstreamAA-347 | SNV_RET_1_Hook2 | /5phos/ATGCTGACGGTCAAGTGGTCTTAGGGTGGTGTAGATATGATCAAAAAGGGATTCAATTGC/3AmMO/ (SEQ ID NO: 8) |
| CNV_PTEN_+_1 | DownstreamAA-406 | CNV_PTEN_1_Hook2 | /5phos/ATGCTGACGGTCAAGTGGTCTTAGGGCTGCAGGAGAAACAGTCTC/3AmMO/ (SEQ ID NO: 9) |

3. 3' End Ligation Reaction

A mixture solution was prepared according to Table 2 below:

TABLE 2

| Component | Amount |
|---|---|
| 10× reaction buffer (Epicentre) | 1 μL |
| 0.025 mM ATP (Epicentre) | 0.5 μL |
| 50 mM MnCl₂ (Epicentre) | 1 μL |
| 100% DMSO (Sigma) | 2 μL |
| Circligase cyclase(100 U/μL) (Epicentre) | 0.2 μL |
| Enzyme-free pure water | 5.3 μL |
| Total volume | 10 μL |

The above mixture solution was added to the hybridization reaction system, mixed well with a pipette, and incubated at 42° C. for 1 h. Note: when adding the mixture solution, the mixture solution was at room temperature, and the hybridization mixture was still in the PCR instrument.

4. Exonuclease Digestion

To each reaction, 1 μL of exonuclease 1 (Exo I, New England Biolabs® Corp.) was added, and mixed well with a pipette, followed by reaction at 37° C. for 30 min and at 80° C. for 20 min.

5. 5' End Ligation Reaction

5' end hybridization: to each reaction, 1 μl of the 5' hook probe at a respective concentration (0.1 μM, 0.01 μM, 0.005 μM, or 0.002 μM) was added, and mixed well with a pipette, followed by reaction in the following procedure: 95° C., 5 min, temperature decrease to 42° C. at a rate of 0.1 sec, 42° C. reaction for 30 min, and storage at 42° C. The design of the 5' hook probe was as follows:

NNNNNNNNNNNNNNNNN<u>GAACGACATGGCTACGATCCGACTT</u>NNNNNNT (SEQ ID NO: 10, the sequence underlined is partial adapter sequence, and the sequence not underlined is the hybridization complementary sequence designed for different ROI regions).

Some probe sequences are shown in Table 3 below.

TABLE 3

| ROI SITE | Position | Primer name | Primer sequence |
|---|---|---|---|
| > Fusion_chr10_61638615_chr10_43609947_CCDC6_-_RET_+ | Upstream | AA-238 Fusion_CCDC6/RET_1_Hook1 | GAATTATTTAACAATTATGACTATTCATTTAGGCGAACGACATGGCTACGATCCGACTTNNNNNT (SEQ ID NO: 11) |
| InDel_chr4_55592185_KIT_+_c.1509_1510insGCCTAT_101 | Upstream | AA-246 InDel_KIT_1_Hook1 | GGCAGAAGTCTTGCCCACATGAACGACATGGCTACGATCCGACTTNNNNNNT (SEQ ID NO: 12) |
| SNV_chr10_43617416_RET_+_c.2753T>C_101_1 | Upstream | AA-346 SNV_RET_1_Hook1 | CATTTAACTGGAATCCGACCCGAACGACATGGCTACGATCCGACTTNNNNNNT (SEQ ID NO: 13) |
| CNV_PTEN_+_1 | Upstream | AA-405 CNV_PTEN_1_Hook1 | CAACAATTCTGGGAACCACCGAACGACATGGCTACGATCCGACTTNNNNNNT (SEQ ID NO: 14) |

5' End Ligation Reaction

A mixture solution was prepared according to Table 4 below:

TABLE 4

| Component | Amount |
| --- | --- |
| 10× reaction buffer (Epicentre) | 0.1 μL |
| 0.025 mM ATP (Epicentre) | 0.5 μL |
| Circligase cyclase (100 U/μL) (Epicentre) | 0.2 μL |
| Enzyme-free pure water | 0.2 μL |
| Total volume | 1 μL |

The above mixture solution was added to the hybridization reaction system, mixed well with a pipette, and incubated at 42° C. for 1 h and at 80° C. for 20 min. Note: when adding the mixture solution, the mixture solution was at room temperature, and the hybridization mixture was still in the PCR instrument.

6. Purification with Magnetic Beads a) 39.6 μL of Ampure XP magnetic beads were added to the above reaction sample (22 μL), and the mixture solution of the magnetic beads and the sample was mixed well by pipetting with a pipette tip for 7-10 times. After allowing binding for 5 min at room temperature, the mixture solution was mixed well by pipetting with a pipette tip for 7-10 times again. And after allowing binding for 5 min at room temperature, the mixture solution was placed on a magnetic stand to allow binding for 2 min (until the liquid became clear), and the supernatant was carefully aspirated and discarded.

b) 180 μL of 70% ethanol was added to the 8-tube strip on the magnetic stand. The tubes were capped tightly and turned upside down for 5 times to mix well, and the supernatant was discarded. Washing was repeated once with 320 μL of 70% ethanol, residual ethanol was discarded as much as possible using a small volume pipette, and the magnetic beads were dried at room temperature.

c) The magnetic beads were resuspended with 20 μL of TE solution, mixed well for 7-10 times by pipetting with a pipette tip. After allowing binding for 5 min at room temperature, mixed well for 7-10 times by pipetting with a pipette tip again. After allowing binding for 5 min at room temperature, the mixture solution was placed on the magnetic stand to allow binding for 2 min (until the liquid became clear). 20 μL of the supernatant was carefully aspirated and transferred to a new 0.2 mL PCR tube for reaction in the next step or for storage at −20° C.

7. PCR Amplification

The reaction mixture shown in Table 5 below was prepared, and 10 μL of the above product was subjected to PCR reaction:

TABLE 5

| Component | Amount |
| --- | --- |
| Ligation product | 10 μL |
| 2× KAPA HiFi HotStart ReadyMix | 12.5 μL |
| 20 μM primer 1 | 0.5 μL |
| 20 μM primer 2 | 0.5 μL |
| Water | 1.5 μL |
| Total volume | 25 μL |

Sequence of primer 1:
(SEQ ID NO: 15)
/5Phos/CACAGAACGACATGGCTACGATCCGACT;

Sequence of primer 2:
(SEQ ID NO: 16)
TGTGAGCCAAGGAGTTGACTTTACTTGTCTTCCTAAGACCACTTGACCGTCAGCAT.

The reaction procedure is as shown in Table 6 below:

TABLE 6

| Temperature--time | Cycle number |
| --- | --- |
| 98° C.--2 min | 1 cycle |
| 98° C.--15 s | 11 cycles |
| 60° C.--15 s | |
| 72° C.--30 s | |
| 72° C.--5 min | 1 cycle |
| 4° C.--maintain | — |

8. Polyacrylamide Gel Electrophoresis

Figure 11:
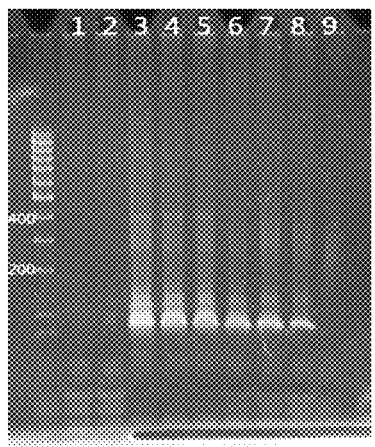
FIG. 11 shows the results of polyacrylamide gel electrophoresis of part of the products in Example 1 of the present invention.

6 μL of the PCR product was subjected to polyacrylamide gel electrophoresis at 240 V for 20 min. The results are as shown in FIG. 11. The results show that:

Lane 1: With only 3' hook probe and DNA, there were no corresponding products after PCR amplification.

Lane 2: With only 5' hook probe and DNA, there were no corresponding products after PCR amplification. It can be known from lane 1 and lane 2 that the hook probes and the PCR primers had good specificity.

Lane 3: With 3' hook probe and 5' hook probe and DNA, there were corresponding products after PCR amplification. However, because the initial dosing amounts were relatively small, the corresponding target products could only be obtained when the number of PCR cycles was relatively large. However, the number of PCR cycles in this reaction was lower than the theoretical value, so the brighter the band in the gel image, the higher the off-target efficiency. In addition, an unknown band of 400 bp would appear in the PCR product.

Lanes 4-6: The concentration of the 3' hook probe was kept unchanged and the concentration of the 5' hook probe was reduced. The results show that for the target band, the total amount of PCR product would decrease with decreasing concentration of the 5' hook probe. This indirectly reflects that the real target product gradually emerged. And when decreasing to a certain concentration, the 400 bp band would disappear. Therefore, subsequent attempt was made to further adjust the concentration of the hook probe.

Lanes 7-8: The concentration of the 5' hook probe was kept constant and the concentration of the 3' hook probe was reduced. The results show that the 400 bp band would also disappear under this condition, but the total amount of the non-specific PCR products also tended to decrease. Therefore, subsequent attempt was made to adjust the concentration of the hook probe to improve the capture efficiency.

Lane 9: With only the DNA template.

Example 2: Target Region Enrichment by Bilateral Hook Probe Hybridization

1. Sample Collection and Processing

Fragmentase was used to fragment the human NA12878 (GM12878, CORIELL INSTITUTE) genomic DNA, and then DNA fragments of 200-400 bp were selected using the double selection method.

2. Denaturing and Hybridization

Preparation of the hybridization reaction system: 10 ng of fragmented human NA12878 (GM12878, CORIELL INSTITUTE) genomic DNA were mixed with 1 μl of a 0.1 μM mixed solution of the 5' hook probe and the 3' hook probe, 1 μL of the reaction buffer was added, and then water was added to make up to 10 μL. The mixture was vortexed well and allowed to react in a PCR instrument in the following procedure: 95° C., 5 min, cooling to 42° C. at a rate of 0.1 sec, 42° C. reaction for 1 h, and storage at 42° C.

The 5' hook probe was designed as follows:
NNNNNNNNNNNNNNNNN<u>GAACGACATGGCTACGATCCGACTT</u>NNNNNNT (SEQ ID NO: 10, the sequence underlined is partial adapter sequence, and the sequence not underlined is the hybridization complementary sequence designed for different ROI regions).

The 3' hook probe was designed as follows:
/5phos/<u>ATGCTGACGGTCAAGTGGTCTTAGG</u>NNNNNNNNNNNNNNNN/3AmMO/(SEQ ID NO: 5, the sequence underlined is partial adapter reverse complementary sequence, and the sequence not underlined is the hybridization complementary sequence designed for different ROI regions).

Some probe sequences are shown in Table 7 below.

TABLE 7

| ROI site | Position | Primer name | Primer sequence |
| --- | --- | --- | --- |
| > Fusion_chr10_61638615_chr10_43609947_CCDC6_-_RET_+ | Upstream | AA-238 Fusion_CCDC6/RET_1_Hook1 | GAATTATTTAACAATTATG ACTATTCATTTAGGCGAAC GACATGGCTACGATCCGA CTNNNNNNT (SEQ ID NO: 11) |
|  | Downstream | AA-239 Fusion_CCDC6/RET_1_Hook2 | /5phos/ATGCTGACGGTCAA GTGGTCTTAGGAGGACAG CGGCTGCGATCAC/3AmMO/ (SEQ ID NO: 6) |
| InDel_chr4_55592185_KIT_+_c.1509_1510insGCCTAT_101 | Upstream | AA-246 InDel_KIT_1_Hook1 | GGCAGAAGTCTTGCCCACA TGAACGACATGGCTACGAT CCGACTTNNNNNNT (SEQ ID NO: 12) |
|  | Downstream | AA-247 InDel_KIT_1_Hook2 | /5phos/ATGCTGACGGTCAAG TGGTCTTAGGTATACCTTTG TTGTTACCTTTAAATGCAAA GTTAA/3AmMO/ (SEQ ID NO: 7) |
| SNV_chr10_43617416_RET_+_c.2753T>C_101_1 | Upstream | AA-346 SNV_RET_1_Hook1 | CATTTAACTGGAATCCGACC CGAACGACATGGCTACGATC CGACTNNNNNNT (SEQ ID NO: 13) |
|  | Downstream | AA-347 SNV_RET_1_Hook2 | /5phos/ATGCTGACGGTCAAGT GGTCTTAGGGTGGTGTAGATA TGATCAAAAAGGGATTCAATT GC/3AmMO/ (SEQ ID NO: 8) |
| CNV_PTEN_+_1 | Upstream | AA-405 CNV_PTEN_1_Hook1 | CAACAATTCTGGGAACCACC GAACGACATGGCTACGATCC GACTNNNNNNT (SEQ ID NO: 14) |
|  | Downstream | AA-406 CNV_PTEN_1_Hook2 | /5phos/ATGCTGACGGTCAAGT GGTCTTAGGGCTGCAGGAGA AACAGTCTC/3AmMO/ (SEQ ID NO: 9) |

3. Bilateral Hook Probe Ligation Reaction

A mixture solution was prepared according to Table 8 below:

TABLE 8

| Component | Amount |
| --- | --- |
| 10× Reaction buffer (Epicentre) | 1 µL |
| 0.025 mM ATP (Epicentre) | 0.5 µL |
| 50 mM MnCl₂ (Epicentre) | 1 µL |
| 100% DMSO (Sigma) | 2 µL |
| Circligase cyclase (100 U/µL) (Epicentre) | 0.2 µL |
| Enzyme-free pure water | 5.3 µL |
| Total volume | 10 µL |

The above mixture solution was added to the hybridization reaction system, mixed well with a pipette, and incubated at 42° C. for 1 h. Note: when adding the mixture solution, the mixture solution was at room temperature, and the hybridization mixture was still in the PCR instrument.

4. Exonuclease Digestion

To each reaction, 1 µL of exonuclease 1 (Exo I, New England Biolabs® Corp.) was added, and mixed well with a pipette, followed by reaction at 37° C. for 30 min and at 80° C. for 20 min.

5. Purification with Magnetic Beads a) 37.8 µL of Ampure XP magnetic beads were added to the above reaction sample (21 µL), and the mixture solution of the magnetic beads and the sample was mixed well by pipetting with a pipette tip for 7-10 times. After allowing binding for 5 min at room temperature, the mixture solution was mixed well by pipetting with a pipette tip for 7-10 times again. And after allowing binding for 5 min at room temperature, the mixture solution was placed on a magnetic stand to allow binding for 2 min (until the liquid became clear), and the supernatant was carefully aspirated and discarded.

b) 180 µL of 70% ethanol was added to the 8-tube strip on the magnetic stand. The tubes were capped tightly and turned upside down for 5 times to mix well, and the supernatant was discarded. Washing was repeated once with 320 µL of 70% ethanol, residual ethanol was discarded as much as possible using a small volume pipette, and the magnetic beads were dried at room temperature.

c) The magnetic beads were resuspended with 20 µL of TE solution, mixed well for 7-10 times by pipetting with a pipette tip. After allowing binding for 5 min at room temperature, the mixture solution was mixed for 7-10 times by pipetting with a pipette tip again. After allowing binding for 5 min at room temperature, the mixture solution was placed on the magnetic stand to allow binding for 2 min (until the liquid became clear). 20 µL of the supernatant was carefully aspirated and transferred to a new 0.2 mL PCR tube for reaction in the next step or for storage at −20° C.

6. PCR Amplification

The reaction mixture shown in Table 9 below was prepared, and 10 µL of the above product was subjected to PCR reaction:

TABLE 9

| Component | Amount |
| --- | --- |
| Ligation product | 10 µL |
| 2× KAPA HiFi HotStart ReadyMix | 25 µL |
| 20 µM Primer 1 | 1 µL |
| 20 µM Primer 2 | 1 µL |
| Water | 13 µL |
| Total volume | 50 µL |

Sequence of primer 1:
(SEQ ID NO: 15)
/5Phos/CACAGAACGACATGGCTACGATCCGACT;

Sequence of primer 2:
(SEQ ID NO: 16)
TGTGAGCCAAGGAGTTGACTTTACTTGTCTTCCTAAGACCACTTGACCGTCAGCAT.

The reaction procedure is as shown in Table 10 below:

TABLE 10

| Temperature—Time | Cycle number |
| --- | --- |
| 98° C.--2 min | 1 cycle |
| 98° C.--15 s | 16 cycles |
| 60° C.--15 s | |
| 72° C.--30 s | |
| 72° C.--5 min | 1 cycle |
| 4° C.--maintain | — |

8. Polyacrylamide Gel Electrophoresis

Figure 12:
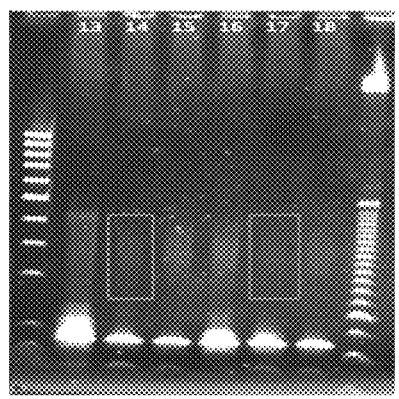
FIG. 12 shows the results of polyacrylamide gel electrophoresis of part of the products in Example 2 of the present invention.
Figure 13:
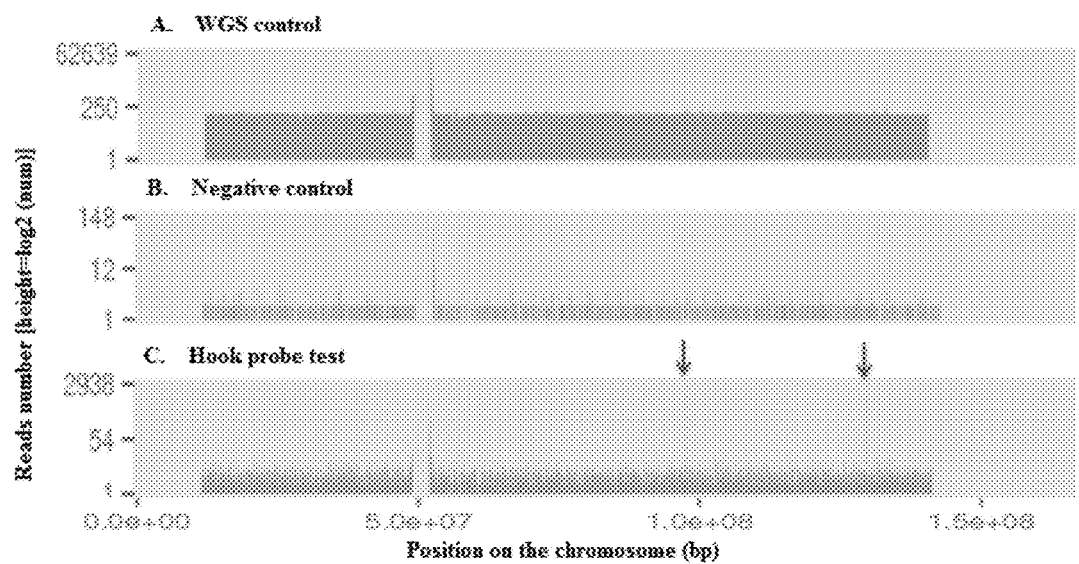
FIG. 13 shows the distribution of sequencing reads on Chromosome 10 in Example 2 of the present invention, wherein A and B respectively represent WGS control library and negative control library, C represents bilateral hook probe hybridization library, with the regions pointed to by the two arrows in FIG. 13C representing two ROIs (regions of interest) enrichment regions.

6 µL of the PCR product was subjected to polyacrylamide gel electrophoresis at 240 V for 20 min. FIG. 12 shows the results of polyacrylamide gel electrophoresis of some products in the present example, in which lane 14 is the electrophoresis result of the library construction product under the library construction condition in the present example 9. PE50 Sequencing Result and Analysis FIG. 13 shows the distribution of the reads on Chromosome 10, in which A and B are respectively WGS control library and negative control library, without visible target region enrichment; and C is bilateral hook probe hybridization library, with two ROIs being enriched significantly.

Figure 14:
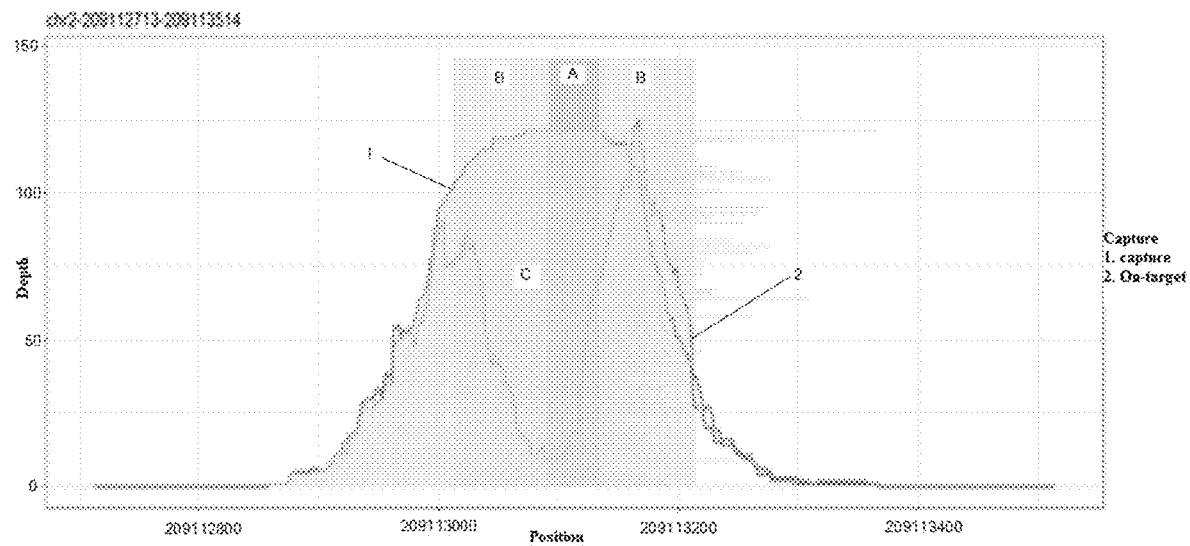
FIG. 14 shows coverage of ROI regions by capture reads and on-target reads in Example 2 of the present invention.

FIG. 14 shows coverage of the ROIs by capture reads and on-target reads respectively, showing that the capture reads markedly covered the ROIs, and the target regions on the chromosome were markedly enriched. The red line (curve 1 in FIG. 14) represents capture reads, the blue line (curve 2 in FIG. 14) represents on-target reads, the dark grey area (represented by A in FIG. 14) is ROI±20 bp, the light grey area (represented by B in FIG. 14) is ROI±100 bp, and the yellow line (represented by C in FIG. 14) shows the length after the PE reads of opposite ends were joined.

The above results indicate that under the conditions of the present example, the PE50 sequencing data gave a good performance in the on target rate and the capture rate.

Example 3: 3' Hook Probe Hybridization Test

1. Sample Collection and Processing

Fragmentase was used to fragment the human NA12878 (GM12878, CORIELL INSTITUTE) genomic DNA, and then DNA fragments of 200-400 bp were selected using the double selection method.

2. Dephosphorylation Reaction 10 ng of fragmented human NA12878 (GM12878, CORIELL INSTITUTE) genomic DNA were added with a suitable amount of rSAP enzyme (New England Biolabs® Corp.), and 1 µL of the reaction buffer was added, and then water was added to make up to 10 µL. The mixture was vortexed well and allowed to react in a PCR instrument in the following procedure: 37° C., 30 min, 65° C. reaction for 15 min, and storage at 42° C.

3. Denaturing and Hybridization

Preparation of the hybridization reaction system: the above dephosphorylation reaction solution was mixed with 1 µL of 0.2 µM of the 3' hook probe, at which time the total volume is 11 µL. The mixture was vortexed well and allowed to react in a PCR instrument in the following procedure: 95° C., 5 min, cooling to 42° C. at a rate of 0.1 sec, 42° C. reaction for 1 h, and storage at 42° C. The 3' hook probe is designed as follows:
/5phos/

ATGCTGACGGTCAAGTGGTCTTAGGNNNNNNNNNN NNNNNNN/3AmMO/(SEQ ID NO: 5, the sequence underlined is partial adapter reverse complementary sequence, and the sequence not underlined is the hybridization complementary sequence designed for different ROI regions).

Some probe sequences are shown in Table 11 below:

TABLE 11

| ROI site | Position | Primer name | Primer sequence |
|---|---|---|---|
| > Fusion_chr10_ 61638615_chr10_ 43609947_CCDC6_-_RET_+ | Downstream | AA-239 Fusion_CCDC6/ RET_1_Hook2 | /5phos/ATGCTGACGGTCAA GTGGTCTTAGGAGGACAG CGGCTGCGATCAC/3AmMO/(SEQ ID NO: 6) |
| InDel_chr4_ 55592185_ KIT_+_c.1509_ 1510insGCCTAT_101 | Downstream | AA-247 InDel_KIT_1_Hook2 | /5phos/ATGCTGACGGTCAAG TGGTCTTAGGTATACCTTTG TTGTTACCTTTAAATGCAAA GTTAA/3AmMO/ (SEQ ID NO: 7) |
| SNV_chr10_ 43617416_RET_+_ c.2753T>C_101_1 | Downstream | AA-347 SNV_RET_1_Hook2 | /5phos/ATGCTGACGGTCAAGT GGTCTTAGGGTGGTGTAGATA TGATCAAAAAGGGATTCAATT GC/3AmMO/ (SEQ ID NO: 8) |
| CNV_PTEN_+_1 | Downstream | AA-406 CNV_PTEN_ 1_Hook2 | /5phos/ATGCTGACGGTCAAGT GGTCTTAGGGCTGCAGGAGA AACAGTCTC/3AmMO/ (SEQ ID NO: 9) |

4. 3' End Ligation Reaction

A mixture solution was prepared according to Table 12 below:

TABLE 12

| Component | Amount |
|---|---|
| 10× Reaction buffer (Epicentre) | 2 μL |
| 0.025 mM ATP (Epicentre) | 0.5 μL |
| 50 mM MnCl$_2$ (Epicentre) | 1 μL |
| 100% DMSO (Sigma) | 1 μL |
| Circligase cyclase (100 U/μL) (Epicentre) | 0.2 μL |
| Enzyme-free pure water | 4.3 μL |
| Total volume | 9 μL |

The above mixture solution was added to the hybridization reaction system, mixed well with a pipette, and incubated at 42° C. for 1 h. Note: when adding the mixture solution, the mixture solution was at room temperature, and the hybridization mixture was still in the PCR instrument.

5. Exonuclease Digestion

To each reaction, 1 μL of exonuclease 1 (Exo I, New England Biolabs® Corp.) was added, and mixed well with a pipette, followed by reaction at 37° C. for 30 min and at 80° C. for 20 min.

6. Primer Extension Reaction

A suitable amount of PE primers carrying different barcodes was introduced. A mixture solution was prepared according to Table 13 below:

TABLE 13

| Component | Amount |
|---|---|
| 2× reaction buffer (Agilent) | 25 μL |
| PfuTurbo Cx Hotstart DNA polymerase (Agilent) | 0.5 μL |
| PE primers (25 μM) | 2 μL |

TABLE 13-continued

| Component | Amount |
|---|---|
| Enzyme-free pure water | 1.5 μL |
| Total volume | 29 μL |

The above mixture solution was added into 21 μL of the exonuclease digestion reaction system, and mixed well with a pipette, followed by being subjected to 98° C. for 3 min, 60° C. for 30 min, and 4° C. storage.

7. Adapter Ligation Reaction

A mixture solution was prepared according to Table 14 below:

TABLE 14

| Component | Amount |
|---|---|
| ATP (NEB Corp.) | 0.8 μL |
| Ligase (NEB Corp.) | 2 μL |
| 10× reaction buffer (NEB Corp.) | 8 μL |
| 50% PEG 8000 | 12 μL |
| Adapter (10 μM) | 1 μL |
| Enzyme-free pure water | 6.2 μL |
| Total volume | 30 μL |

```
Short strand of the adapter:
                        (SEQ ID NO: 17)
GCTACGATCCGACT/ddT/;

Long strand of the adapter:
                        (SEQ ID NO: 18)
/Phos/AAGTCGGATCGTAGCCATGTCGTT/ddC/.
```

The above mixture solution was added into 50 μL of the primer extension reaction system, and mixed well with a pipette, followed by being subjected to 37° C. for 30 min, and 4° C. storage.

8. Purification with Magnetic Beads a) 40 µL of Ampure XP magnetic beads were added to the above reaction sample (80 µL), and the mixture solution of the magnetic beads and the sample was mixed well by pipetting with a pipette tip for 7-10 times. After allowing binding for 5 min at room temperature, the mixture solution was mixed well by pipetting with a pipette tip for 7-10 times again. And after allowing binding for 5 min at room temperature, the mixture solution was placed on a magnetic stand to allow binding for 2 min (until the liquid became clear), and the supernatant was carefully aspirated and discarded.

b) 180 µL of 70% ethanol was added to the 8-tube strip on the magnetic stand. The tubes were capped tightly and turned upside down for 5 times to mix well, and the supernatant was discarded. Washing was repeated once with 320 µL of 70% ethanol, residual ethanol was discarded as much as possible using a small volume pipette, and the magnetic beads were dried at room temperature.

c) The magnetic beads were resuspended with 20 µL of TE solution, mixed well for 7-10 times by pipetting with a pipette tip. After allowing binding for 5 min at room temperature, the mixture solution was mixed for 7-10 times by pipetting with a pipette tip again. After allowing binding for 5 min at room temperature, the mixture solution was placed on the magnetic stand to allow binding for 2 min (until the liquid became clear). 20 µL of the supernatant was carefully aspirated and transferred to a new 0.2 mL PCR tube for reaction in the next step or for storage at −20° C.

9. PCR Amplification

A reaction mixture was prepared according to Table 15, and 20 µL of the above purification product was subjected to PCR reaction:

TABLE 15

| Component | Amount |
| --- | --- |
| Ligation product | 20 µL |
| 2× KAPA HiFi HotStart ReadyMix | 25 µL |
| 20 µM Primer 3 | 2 µL |
| 20 µM Primer 4 | 2 µL |
| Water | 1 µL |
| Total volume | 50 µL |

```
Primer 3:
                                  (SEQ ID NO: 19)
/5Phos/GAACGACATGGCTACGA;

Primer 4:
                                  (SEQ ID NO: 20)
TGTGAGCCAAGGAGTTG.
```

The reaction procedure is as shown in Table 16 below:

TABLE 16

| Temperature--time | Cycle number |
| --- | --- |
| 98° C.--2 min | 1 cycle |
| 98° C.--15 s | 15 cycles |

TABLE 16-continued

| Temperature--time | Cycle number |
| --- | --- |
| 60° C.--15 s | |
| 72° C.--30 s | |
| 72° C.--5 min | 1 cycle |
| 4° C.--maintain | — |

10. Polyacrylamide Gel Electrophoresis

Figure 15:
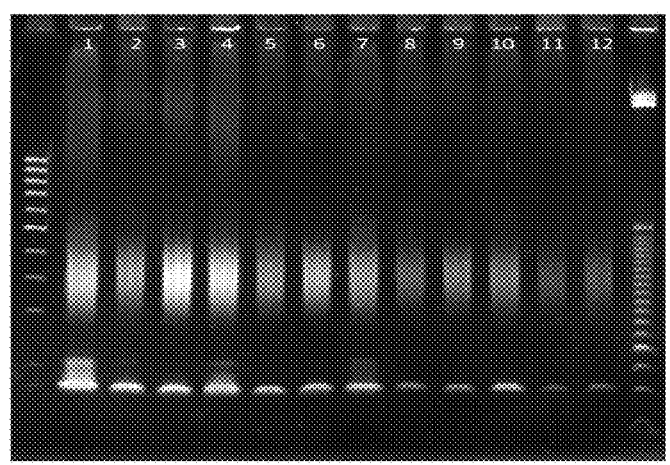
FIG. 15 shows the results of polyacrylamide gel electrophoresis of part of the products in Example 3 of the present invention.

6 µL of the PCR product was subjected to polyacrylamide gel electrophoresis at 240 V for 20 min. FIG. 15 shows the results of polyacrylamide gel electrophoresis of some products in the present example, in which lane 12 is the electrophoresis result of the library construction product under the library construction condition in the present example Moreover, the library of the present example was subjected to PESO sequencing and analysis, which shows that the PESO sequencing data gave a good performance in the on target rate and the capture rate.

The present invention has been described above with reference to specific examples, which are merely intended to aid the understanding of the present invention and are not intended to limit the present invention thereto. Several simple derivations, variations or substitutions can be made by a person skilled in the art to which the present invention pertains in light of the concept of the present invention. For example, examples of typical but not limiting derivations, variations or substitutions include the following: the hook probe can not only be designed as a DNA probe, but also be designed as an RNA probe. The hybridization complex for intermolecular ligation can be one or more of DNA/DNA, DNA/RNA, and RNA/RNA hybridization complexes. Removal of potential intermolecular non-specific linear ligation products can also be achieved by other possible means besides single-stranded exonuclease treatment, such as gel recovery or magnetic bead selection. In the monolateral hook probe protocol, adapter ligation at the non-monolateral hook probe hybridization ligation end is possible with other alternative methods, beside the method described herein. In order to enhance the effect of target nucleic acid enrichment, the effect can be improved by altering the hybridization system, the hybridization components, the hybridization reagents, the hybridization temperatures, among other reaction conditions, and can also be achieved by way of secondary or multiple nested enrichment. As described herein, the present invention is not limited to high-throughput library construction techniques and kit development, but can also be applied to molecular cloning experiments such as RACE, to synthetic biology experiments such as joining of artificially synthesized sequences and development of corresponding kits, to gene typing, fluorescent quantitative PCR, and other biochemical experiments that rely on chemiluminescence for showing detection results, as well as kit development, and to any applications in which a stretch of known nucleic acid sequence is needed to detect or extract the information of a known sequence or the flanking sequences of the known sequence, or in which a known sequence is used to mediate the addition of another sequence into a known sequence fragment or the flanking fragments of the known sequence fragment.

The invention claimed is:

1. A method for nucleic acid sequencing library construction, the method comprising:
   (i) a step of annealing and hybridizing a hook probe to a denatured nucleic acid fragment to be ligated, the hook probe comprising a target-specific region and a hook region, the hook region consisting of a single strand of nucleic acids, the target-specific region comprising a sequence complementary to at least part of a single strand of a nucleic acid fragment to be ligated, the hook region comprising a sequence not complementary to the nucleic acid fragment, and an end of the hook region being a ligatable end, which can be ligated to a single-stranded end of the nucleic acid fragment; and
   (ii) a step of ligating the ligatable end of the hook probe to a single-stranded end of the nucleic acid fragment in the presence of a ligase.

2. The method for nucleic acid sequencing library construction according to claim 1, wherein the method further comprises:
   a step of removing linear non-specific ligation products, excess nucleic acid fragments and excess hook probes.

3. The method for nucleic acid sequencing library construction according to claim 1, wherein the method further comprises:
   a step of subjecting the ligation product of the hook probe and the nucleic acid fragment to PCR amplification using universal primers.

4. The method for nucleic acid sequencing library construction according to claim 1, wherein the hook region comprises a restriction enzyme binding site cleavable with a restriction enzyme and/or one or more modified nucleotides that are cleavable, and the method further comprises:
   a step of subjecting the restriction enzyme binding site to restriction enzyme cleavage using a restriction enzyme and/or cleaving the one or more modified nucleotides using a cleaving enzyme.

5. The method for nucleic acid sequencing library construction according to claim 1, wherein the hook probe includes a 5' hook probe and a 3' hook probe, the 5' hook probe has the structure of 5'-(target specific region)-(hook region)-3', the 3' end of the hook region of the 5' hook probe has a functional 3' hydroxy group capable of being ligated to the 5' end of the nucleic acid fragment; the 3' hook probe has the structure of 5'-(hook region)-(target specific region)-3', the 5' end of the hook region of the 3' hook probe has a functional 5' phosphate group capable of being ligated to the 3' end of the nucleic acid fragment; the target specific region of the 5' hook probe comprising a sequence complementary to at least a first part of the denatured nucleic acid fragment to be ligated, the target specific region of the 3' hook probe comprising a sequence complementary to at least a second part of the denatured nucleic acid fragment to be ligated, and the hook region of the 5' hook probe and the hook region of the 3' hook probe respectively comprise a universal primer binding site; and the method specifically comprises the following steps:

annealing and hybridizing the respective 5' and 3' hook probes to the denatured nucleic acid fragment to be ligated such that the respective sequences of the 5' hook probe and 3' hook probe, when annealed and hybridized to the respective at least first and second parts of the denatured nucleic acid fragment to which they are complementary, are spaced from respective ends of the denatured nucleic acid fragment;

in the presence of the ligase, ligating the functional 3'-hydroxy group of the 5' hook probe to the 5' end of the nucleic acid fragment, and ligating the functional 5'-phosphate group of the 3' hook probe to the 3' end of the nucleic acid fragment;

digesting the linear non-specific ligation products, excess nucleic acid fragments and excess hook probes using a single-stranded exonuclease; and subjecting the ligation product of the hook probes and the nucleic acid fragment to PCR amplification using universal primers, wherein the universal primers are respectively complementary to the universal primer binding sites of the 5' hook probe and the 3' hook probe.

6. The method for nucleic acid sequencing library construction according to claim 1, wherein the hook probe includes a 5' hook probe and a 3' hook probe, the 5' hook probe has the structure of 5'-(target specific region)-(hook region)-3', the 3' end of the hook region of the 5' hook probe has a functional 3' hydroxy group capable of being ligated to the 5' end of the nucleic acid fragment; the 3' hook probe has the structure of 5'-(hook region)-(target specific region)-3', the 5' end of the hook region of the 3' hook probe has a functional 5' phosphate group capable of being ligated to the 3' end of the nucleic acid fragment; and the hook region of the 5' hook probe and the hook region of the 3' hook probe respectively comprise a restriction enzyme binding site cleavable with a restriction enzyme and/or one or more modified nucleotides that are cleavable; and the method specifically comprises the following steps:

annealing and hybridizing the respective 5' and 3' hook probes to the denatured nucleic acid fragment to be ligated;

in the presence of the ligase, ligating the functional 3'-hydroxy group of the 5' hook probe to the 5' end of the nucleic acid fragment, and ligating the functional 5'-phosphate group of the 3' hook probe to the 3' end of the nucleic acid fragment;

digesting the linear non-specific ligation products, excess nucleic acid fragments and excess hook probes using a single-stranded exonuclease; and subjecting the restriction enzyme binding site to restriction enzyme cleavage using a restriction enzyme and/or cleaving the one or more modified nucleotides using a cleaving enzyme.

7. The method for nucleic acid sequencing library construction according to claim 1, wherein the hook probe includes a 3' hook probe, the 3' hook probe has the structure of 5'-(hook region)-(target specific region)-3', the 5' end of the hook region of the 3' hook probe has a functional 5'-phosphate group capable of being ligated to the 3'-end of the nucleic acid fragment; and the method specifically comprises the following steps:

annealing and hybridizing the hook probe to the denatured nucleic acid fragment to be ligated;

in the presence of a ligase, ligating the functional 5'-phosphate group of the 3' hook probe to the 3' end of the nucleic acid fragment;

digesting the linear non-specific ligation products, excess nucleic acid fragments and excess hook probes using a single-stranded exonuclease;

performing a primer extension reaction using primer sequences completely or partly complementary to the hook region sequence of the 3' hook probe;

connecting a 5'-adapter to the 5'-end of the product of the extension reaction; and performing PCR amplification using primer sequences completely or partly complementary to the 5' adapter and the hook region sequence of the 3' hook probe.

8. The method for nucleic acid sequencing library construction according to claim 1, wherein the hook probe includes a 3' hook probe, the 3' hook probe has the structure of 5'-(hook region)-(target specific region)-3', the 5' end of the hook region of the 3' hook probe has a functional 5'-phosphate group capable of being ligated to the 3'-end of the nucleic acid fragment; the hook region of the 3' hook probe comprises a restriction enzyme binding site cleavable with a restriction enzyme and/or one or more modified nucleotides that are cleavable; and the method specifically comprises the following steps:

annealing and hybridizing the hook probe to the nucleic acid fragment to be ligated;

in the presence of a ligase, ligating the functional 5'-phosphate group of the 3' hook probe to the 3' end of the nucleic acid fragment;

digesting the linear non-specific ligation products, excess nucleic acid fragments and excess hook probes using a single-stranded exonuclease; and subjecting the restriction enzyme binding site to restriction enzyme cleavage using a restriction enzyme and/or cleaving the one or more modified nucleotides using a cleaving enzyme.

9. The method for nucleic acid sequencing library construction according to claim 1, wherein the hook probe includes a 3' hook probe, the 3' hook probe has the structure of 5'-(hook region)-(target specific region)-3', the 5' end of the hook region of the 3' hook probe has a functional 5'-phosphate group capable of being ligated to the 3'-end of the nucleic acid fragment; the nucleic acid fragment comprises a target region sequence; and the method specifically comprises the following steps:

annealing and hybridizing the hook probe to the denatured nucleic acid fragment to be ligated;

in the presence of a ligase, ligating the functional 5'-phosphate group of the 3' hook probe to the 3' end of the nucleic acid fragment;

digesting the linear non-specific ligation products, excess nucleic acid fragments and excess hook probes using a single-stranded exonuclease;

performing a primer extension reaction using primer sequences completely or partly complementary to the target region sequence or an adjacent region thereof;

connecting a 5'-adapter to the 5'-end of the product of the extension reaction; and
    performing PCR amplification using primer sequences completely or partly complementary to the 5' adapter and the hook region sequence of the 3' hook probe.

10. The method for nucleic acid sequencing library construction according to claim 1, wherein the hook probe includes a 5' hook probe, the 5' hook probe has the structure of 5'-(target specific region)-(hook region)-3', the 3' end of the hook region of the 5' hook probe has a functional 3'-hydroxy group capable of being ligated to the 5'-end of the nucleic acid fragment; the hook region of the 5' hook probe comprises a universal primer binding site; wherein the denatured nucleic acid fragment is prepared by
    subjecting a double-stranded precursor nucleic acid fragment to end repair and dephosphorylation treatment;
    connecting a 3'-adapter to the 3'-end of the end-repaired and dephosphorylated double-stranded precursor nucleic acid fragment, the 3' adapter having a universal primer binding site; and
    denaturing the double-stranded precursor nucleic acid fragment to form the denatured nucleic acid fragment with a connected 3' adapter; and
    wherein the method specifically comprises the following steps:
    annealing and hybridizing the hook probe to the denatured nucleic acid fragment with the connected 3' adapter;
    after phosphorylation treatment, in the presence of a ligase, ligating the functional 3' hydroxy group of the 5' hook probe to the 5' end of the denatured nucleic acid fragment with connected 3' adapter;
    digesting the linear non-specific ligation products, excess nucleic acid fragments and excess hook probes using a single-stranded exonuclease; and
    subjecting the ligation product of the hook probe and the denatured nucleic acid fragment with connected 3' adaptor to PCR amplification using universal primers, wherein the universal primers are respectively complementary to the universal primer binding sites of the 5' hook probe and the 3' adapter.

11. The method for nucleic acid sequencing library construction according to claim 1, wherein the hook probe includes a 5' hook probe, the 5' hook probe has the structure of 5'-(target specific region)-(hook region)-3', the 3' end of the hook region of the 5' hook probe has a functional 3'-hydroxy group capable of being ligated to the 5'-end of the nucleic acid fragment; the hook region of the 5' hook probe comprises a restriction enzyme binding site cleavable with a restriction enzyme and/or one or more modified nucleotides that are cleavable; wherein the denatured nucleic acid fragment is prepared by the following steps:
    subjecting a double-stranded precursor nucleic acid fragment to be ligated to end repair and dephosphorylation treatment;
    connecting a 3'-adapter to the 3'-end of the end-repaired and dephosphorylated double-stranded precursor nucleic acid fragment, the 3' adapter comprising a restriction enzyme binding site cleavable with a restriction enzyme and/or one or more modified nucleotides that are cleavable;
    denaturing the double-stranded precursor nucleic acid fragment to form the denatured nucleic acid fragment with a connected 3'-adapter; and
    wherein the method specifically comprises the following steps:
    annealing and hybridizing the hook probe to the denatured nucleic acid fragment with the connected 3' adapter;
    after phosphorylation treatment, in the presence of a ligase, ligating the functional 3' hydroxy group of the 5' hook probe to the 5' end of the denatured nucleic acid fragment with connected 3' adapter;
    digesting the linear non-specific ligation products, excess nucleic acid fragments and excess hook probes using a single-stranded exonuclease; and
    subjecting the restriction enzyme binding site to restriction enzyme cleavage using a restriction enzyme and/or cleaving the one or more modified nucleotides using a cleaving enzyme.

12. The method for nucleic acid sequencing library construction according to claim 1, wherein the hook probe includes a 3' hook probe, the 3' hook probe has the structure of 5'-(hook region)-(target specific region)-3', the 5' end of the hook region of the 3' hook probe has a functional 5'-phosphate group capable of being ligated to the 3'-end of the nucleic acid fragment; and the method specifically comprises the following steps:
    annealing and hybridizing the hook probe to the denatured nucleic acid fragment to be ligated;
    in the presence of a ligase, ligating the functional 5'-phosphate group of the 3' hook probe to the 3' end of the nucleic acid fragment;
    in the presence of a polymerase, performing an extension reaction with the 3' end of the 3' hook probe as the reaction start point for the polymerase;
    digesting the linear non-specific ligation products, excess nucleic acid fragments and excess hook probes using a single-stranded exonuclease;
    connecting a 5'-adapter to the 5'-end of the product of the extension reaction; and
    performing PCR amplification using primer sequences completely or partly complementary to the 5' adapter and the hook region sequence of the 3' hook probe.

13. The method for nucleic acid sequencing library construction according to claim 1, wherein the method further comprises: digesting the linear non-specific ligation products, excess nucleic acid fragments and excess hook probes using a single-stranded exonuclease.

14. The method for nucleic acid sequencing library construction according to claim 5, wherein the sequences of the 5' hook probe that are complementary to the at least first part of the denatured nucleic acid fragment are complementary to sequences of the denatured nucleic acid fragment that are spaced at least 4 nucleotides from the end of the denatured nucleic acid fragment.

* * * * *